(12) United States Patent
Nakamura et al.

(10) Patent No.: US 8,637,710 B2
(45) Date of Patent: Jan. 28, 2014

(54) CATALYST FOR CROSS-COUPLING REACTION COMPRISING UNSUBSTITUTED OR SUBSTITUTED BISPHOSPHINOBENZENES

(75) Inventors: Masaharu Nakamura, Uji (JP); Takuji Hatakeyama, Uji (JP); Yu-ichi Fujiwara, Uji (JP)

(73) Assignee: Kyoto University, Kyoto-shi (JP)

(*) Notice: Subject to any disclaimer, the term of this patent is extended or adjusted under 35 U.S.C. 154(b) by 36 days.

(21) Appl. No.: 12/737,288

(22) PCT Filed: Mar. 10, 2009

(86) PCT No.: PCT/JP2009/054588
§ 371 (c)(1),
(2), (4) Date: Mar. 7, 2011

(87) PCT Pub. No.: WO2010/001640
PCT Pub. Date: Jan. 7, 2010

(65) Prior Publication Data
US 2011/0152523 A1     Jun. 23, 2011

(30) Foreign Application Priority Data

Jul. 2, 2008 (JP) ................................ 2008-174021

(51) Int. Cl.
  *G07F 9/02* (2006.01)
(52) U.S. Cl.
  USPC ......................................................... 568/17
(58) Field of Classification Search
  USPC ......................................................... 568/17
  See application file for complete search history.

(56) References Cited

U.S. PATENT DOCUMENTS

| 5,789,624 A * | 8/1998 | Unruh et al. .................. 568/454 |
| 7,781,599 B2 | 8/2010 | Nakamura et al. |
| 2007/0123734 A1 | 5/2007 | Nakamura et al. |

FOREIGN PATENT DOCUMENTS

| JP | 01289805 A | 11/1989 |
| WO | WO-2005/075384 A1 | 8/2005 |

OTHER PUBLICATIONS

Brunner, et al. Synthesis, 11, 1997, 1309-1314.*
Takayuki Kondo et al., "Fluoro Allyl Kinzoku Hannozai to Hologen-ka Alkyl tono Tetsu Shokubai ni yoru Cross Coupling Hanno," CSJ: The Chemical Society of Japan Koen Yokoshu, Mar. 12, 2007, vol. 87th, No. 2, p. 1061 and Information Sheet.
Masao Iwamoto, et al., "Reaction of Butadiene with Ethylene. II. New Catalytic Systems in Synthesis of 1, 4-Hexadiene," Journal of Organic Chemistry, vol. 31, No. 12, 1966, pp. 4290-4291.
Rosa, P. et al., "Heat-and light-induced spin transition of an iron (II) polymer containing the 1,2,4,5-tetrakis(diphenylphosphanyl) benzene ligand," European Journal of Inorganic Chemistry, 2004, No. 15, pp. 3017-3019.
T. Nagano, et al., "Iron-Catalyzed Grignard Cross-Coupling with Alkyl Halides Possessing β-Hydrogens," Organic Letters, 2004, vol. 6, No. 8, pp. 1297-1299.
R. Martin, et al., "Cross-Coupling of Alkyl Halides with Aryl Grignard Reagents Catalyzed by a Low-Valent Iron Complex," Angew. Chem. Int. Ed. 2004, 43, pp. 3955-3957.
R. B. Bedford, et al., "Iron-Phosphine, -Phosphite, -Arsine, and -Carbene Catalysts for the Coupling of Primary and Secondary Alkyl Halides with Aryl Grignard Reagents," J. Org. Chem. 2006, 71, pp. 1104-1110.
H. Yao, et. al., "Quantum Dot/Bioluminescence Resonance Energy Transfer Based Highly Sensitive Detection of Proteases," Angew. Chem. Int. Ed. 2007, 46, pp. 4346-4349.
C. M. R. Voila, et. al., "Iron-Catalyzed Desulfinylative C-C Cross-Coupling Reactions of Sulfonyl Chlorides with Grignard Reagents," Angew. Chem. Int. Ed. 2008, 47, pp. 1305-1307.
M. Nakamura, et al., "Iron-Catalyzed Chemoselective Cross-Coupling of Primary and Secondary Alkyl Halides with Arylzinc Reagents," Synlett 2005, No. 11, pp. 1794-1798.
M. Nakamura, et al., "Iron-Catalyzed Cross-Coupling of Primary and Secondary Alkyl Halides with Aryl Grignard Reagents" J. Am. Chem. Soc. 2004, 126, pp. 3686-3687.
International Search Report dated Jun. 2, 2009, issued for PCT/JP2009/054588.
Takayuki Kondo et al., "Fluoro Allyl Kinzoku Hannozai to Hologen-ka Alkyl tono Tetsu Shokubai ni yoru Cross Coupling Hanno (Iron-Catalyzed Cross-Coupling Reaction of Fluoroaryl Metal Reagents with Alkyl Halides)," CSJ: The Chemical Society of Japan Koen Yokoshu, Mar. 12, 2007, vol. 87th, No. 2, p. 1061, an Information Sheet and English translation thereof.

(Continued)

*Primary Examiner* — Douglas M Willis
(74) *Attorney, Agent, or Firm* — Edwards Wildman Palmer LLP; James E. Armstrong, IV

(57) ABSTRACT

The present invention provides a process for efficiently producing an alkylated aromatic compound in good yield, by a cross-coupling reaction between an alkyl halide and an aromatic magnesium reagent. A process for producing an aromatic compound represented by Formula (1):

$$R\text{—}Ar' \qquad (1)$$

wherein R is a hydrocarbon group, and Ar' is an aryl group; the process comprising:
reacting a compound represented by Formula (2):

$$R\text{—}X \qquad (2)$$

wherein X is a halogen atom, and R is as defined above, with a magnesium reagent represented by Formula (3):

$$Ar'\text{—}MgY \qquad (3)$$

wherein Y is a halogen atom, and Ar' is as defined above, in the presence of a catalyst for cross-coupling reactions comprising an iron compound and a bisphosphine compound represented by Formula (4):

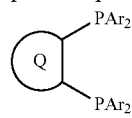

(4)

wherein Q is a divalent group derived from an aromatic ring by removing two hydrogen (H) atoms on adjacent carbon atoms; and each Ar is independently an aryl group.

3 Claims, 4 Drawing Sheets

(56) References Cited

OTHER PUBLICATIONS

M. J. Overett et al. "Carbon-bridged diphosphine ligands for chromium—catalysed ethylene tetramerisation and trimerisation reactions,"Journal of Molecular Catalysts A: Chemical 283 (2008) 114-119.

A. D. Hunter et al. " Bis[ 1,2-bis(p-ethylbenzene)phosphino] benzene," Acta Crystallographica, Section E: Structure Reports Online, vol. E59, No. 11, pp. 01719-01720 (2003).

O. Kaufhold et al. "Template controlled synthesis of a coordinated [11]ane-$P_2C^{NHC}$ macrocycle",Chemical Communications, No. 18, pp. 1822-1824 (2007).

J. N. Dennett et al. "Diphosphine Complexes of Nickel (II) Are Efficient Catalysts for the Polymerization and Oligomerization of Ethylene: Steric Activation and Ligand Backbone Effects," Organometallics, vol. 23, No. 26, pp. 6077-6079, (2004).

Q. Shen et al. "Lewis Acid Acceleration of C-N Bond Forming Reductive Elimination from Heteroarylpalladium Complexes and Catalytic Amidation of Heteroaryl Bromides," Journal of the American Chemical Society, vol. 129 , No. 25, pp. 7734-7735, (2007).

* cited by examiner

Figure 2

| | |
|---|---|
| Molecular Formula | $C_{62}H_{88}Cl_2FeP_2$ |
| Formula Weight | 1022.08 |
| Crystal Dimensions | 0.40 x 0.2 x 0.1 mm |
| Crystal Color, Habit | colorless, platelet |
| Crystal System | monoclinic |
| Lattice Type | C-centered |
| Space Group | C2/c (#15) |
| Lattice Parameters | $a$ = 27.612(7) Å |
| | $b$ = 19.743(4) Å |
| | $c$ = 24.692(6) Å |
| | $\beta$ = 105.9441(16) º |
| | $V$ = 12943(5) Å$^3$ |
| $Z$ value | 8 |
| $D_{calc}$ | 1.049 g/cm$^3$ |
| Radiation | MoK$\alpha$ (l = 0.71070 Å) |
| | graphite monochromated |
| $\mu$ (MoK$\alpha$) | 3.973 cm$^{-1}$ |
| $2\theta_{max}$ | 55.0 º |
| No. of Reflections Measured | Total: 27248 |
| | Unique: 14576 ($R_{int}$ = 0.048) |
| No. Variables | 605 |
| Reflection/Parameter Ratio | 24.09 |
| Residuals: $R_1$ (I>2.00s(I)) | 0.1013 |
| Residuals: $R$ (All reflections) | 0.1568 |
| Residuals: $wR_2$ (All reflections) | 0.3458 |
| Goodness of Fit Indicator | 1.096 |
| Max Shift/Error in Final Cycle | 0.001 |
| Structure Solution | Direct Methods (SHELX97) |

Figure 4

| | |
|---|---|
| Molecular Formula | $C_{38}H_{40}Cl_2FeP_2$ |
| Formula Weight | 685.43 |
| Crystal Dimensions | 0.30 x 0.15 x 0.05 mm |
| Crystal Color, Habit | colorless, platelet |
| Crystal System | monoclinic |
| Lattice Type | Primitive |
| Space Group | $P2_1/m$ (#11) |
| Lattice Parameters | $a$ = 8.94(5) Å |
| | $b$ = 21.32(12) Å |
| | $c$ = 10.21(5) Å |
| | $\beta$ = 99.04(4) º |
| | $V$ = 1921(19) Å$^3$ |
| Z value | 2 |
| $D_{calc}$ | 1.185 g/cm$^3$ |
| Radiation | MoKα (l = 0.71070 Å) |
| | graphite monochromated |
| $\mu$ (MoKα) | 6.374 cm$^{-1}$ |
| $2\theta_{max}$ | 54.7 º |
| No. of Reflections Measured | Total: 10572 |
| | Unique: 4333 ($R_{int}$ = 0.135) |
| No. Variables | 219 |
| Reflection/Parameter Ratio | 19.98 |
| Residuals: $R_1$ (I>2.00s(I)) | 0.1380 |
| Residuals: $R$ (All reflections) | 0.1784 |
| Residuals: $wR_2$ (All reflections) | 0.3890 |
| Goodness of Fit Indicator | 1.001 |
| Max Shift/Error in Final Cycle | 0.000 |
| Structure Solution | Direct Methods (SHELX97) |

CATALYST FOR CROSS-COUPLING REACTION COMPRISING UNSUBSTITUTED OR SUBSTITUTED BISPHOSPHINOBENZENES

CROSS-REFERENCE TO RELATED APPLICATIONS

This application is a 371 US National Phase Application of PCT/JP2009/054588, filed Mar. 10, 2009, which claims priority to Japanese Patent Application No. JP 2008-174021, filed Jul. 2, 2008, the disclosures of each of which are expressly incorporated herein by reference in their entireties.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

INCORPORATION-BY-REFERENCE OF MATERIAL SUBMITTED ON A COMPACT DISC

Not Applicable.

BACKGROUND OF THE INVENTION

1. Field of the Invention

The present invention relates to processes for preparing novel catalysts comprising an iron compound and a bisphosphine compound, and to processes for producing aromatic compounds by coupling halogenated hydrocarbons and aromatic metal reagents using these catalysts.

2. Description of Related Art

Alkylated aromatic compounds, and in particular, a class of aromatic compounds having secondary alkyl groups on their aromatic rings, are known to be useful as starting materials for liquid crystals, or as chemical intermediates for pharmaceuticals, agrochemicals, and the like.

Recently, research into cross-coupling reactions between alkyl halides and aromatic metal reagents is actively taking place. In particular, reports have been made on cross-coupling reactions using iron catalysts, which are inexpensive and readily available (e.g., Non-Patent Documents 1-8, and Patent Document 1).

For example, Patent Document 1 and Non-Patent Document 7 disclose processes wherein cross-coupling reactions between alkyl halides and aromatic magnesium reagents are conducted in the presence of iron (III) chloride and N,N,N',N'-tetramethylethylenediamine (TMEDA). However, these processes require a relatively large proportion, i.e., about 5 mol %, of the iron catalyst relative to the alkyl halide, which is the substrate; therefore, there is still room for improvement in terms of cost and reaction efficiency. Furthermore, substitution of aromatic rings with fluorine atoms is often carried out from the viewpoint of imparting a variety of functionalities to cross-coupling compounds. However, this method is not sufficient for producing a variety of functional compounds because cross-coupling reactions do not proceed at all when using aromatic magnesium reagents having fluorine atoms on their aromatic rings.

Non-Patent Document 8 discloses a process wherein a cross-coupling reaction between an alkyl halide and an aromatic zinc reagent is conducted in the presence of iron (III) chloride and 1,2-bis(diphenylphosphino)benzene (DPPBz). This process also requires a relatively large proportion, i.e., about 3 mol %, of the iron catalyst relative to the alkyl halide; therefore, there is still room for improvement in terms of cost and reaction efficiency.

For these reasons, there has been a need for a process that does not place limitations on the structure of the substrate, and that can efficiently produce a variety of cross-coupling compounds.

Patent Document 1: WO 2005/075384
Non-Patent Document 1: *Org. Lett.*, 6, 1297 (2004)
Non-Patent Document 2: *Angew. Chem., Int. Ed.*, 43, 3955 (2004)
Non-Patent Document 3: *J. Org. Chem.*, 71, 1104 (2006)
Non-Patent Document 4: *Angew. Chem., Int. Ed.*, 46, 4346 (2007)
Non-Patent Document 5: *Angew. Chem., Int. Ed.*, 47, 1305-1307 (2008)
Non-Patent Document 6: *Synlett*, 1794 (2005)
Non-Patent Document 7: *J. Am. Chem. Soc.*, 126, 3686-3687 (2004)
Non-Patent Document 8: Chemical Society of Japan, *Proceedings of the* 87th Annual Spring Meeting, 1D8-12

BRIEF SUMMARY OF THE INVENTION

Problem to be Solved by the Invention

An object of the present invention is to provide processes for efficiently producing alkylated aromatic compounds in good yield, by cross-coupling reactions between alkyl halides and aromatic metal reagents.

Means for Solving the Problem

As a result of extensive research in view of the above-mentioned object, the present inventors found that the object can be achieved by subjecting an alkyl halide and an aromatic magnesium reagent to a cross-coupling reaction in the presence of iron (III) chloride and a bisphosphine compound such as 1,2-bis(di(substituted phenyl)phosphino)benzene. The inventors conducted further research based on this finding, and consequently accomplished the invention. This invention is hereinafter denoted as a "first embodiment".

In summary, the present invention provides, among others, a process for producing an alkylated aromatic compound, as given below.

Item 1. A process for producing an aromatic compound represented by Formula (1):

$$R\text{—}Ar' \tag{1}$$

wherein R is an optionally substituted hydrocarbon group, and may have a group represented by —O— between a carbon-carbon bond of the hydrocarbon group; and Ar' is an optionally substituted aryl or heteroaryl group;

the process comprising:
reacting a compound represented by Formula (2):

  (2)

wherein X is a halogen atom, and R is as defined above, with a magnesium reagent represented by Formula (3):

  (3)

wherein Y is a halogen atom, and Ar' is as defined above,
in the presence of a catalyst for cross-coupling reactions comprising an iron compound and a bisphosphine compound represented by Formula (4):

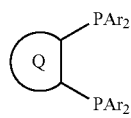  (4)

wherein Q is a divalent group derived from an optionally substituted aromatic or heteroaromatic ring by removing two hydrogen (H) atoms on adjacent carbon atoms; and each Ar is independently an optionally substituted aryl or heteroaryl group.

Item 2. The process according to Item 1, wherein the iron compound is a divalent or trivalent iron salt, or a solvate thereof.

Item 3. The process according to Item 1 or 2, wherein each Ar in Formula (4) above is a group represented by the formula:

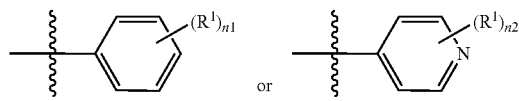

wherein each $R^1$ is independently H, F, an alkyl, alkoxy, aryl, aralkyl, trialkylsilyl, dialkylarylsilyl, alkyldiarylsilyl, or triarylsilyl group; n1 is an integer of 1 to 5; and n2 is an integer of 1 to 4.

Item 4. The process according to Item 1 or 2, wherein each Ar in Formula (4) above is a group represented by the formula:

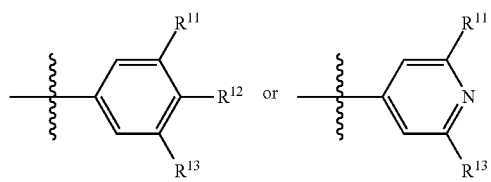

wherein $R^{11}$, $R^{12}$, and $R^{13}$ are each independently H, a $C_1$-$C_6$ alkyl, $C_1$-$C_6$ alkoxy, or trialkylsilyl group, with the proviso that not all of $R^{11}$, $R^{12}$, and $R^{13}$ are H.

Item 5. The process according to Item 4, wherein each Ar in Formula (4) above is a group wherein $R^{12}$ is H; and $R^{11}$ and $R^{13}$ are each independently a $C_1$-$C_6$ alkyl, or trialkylsilyl group.

Item 6. The process according to any one of Items 1 to 5, wherein Q in Formula (4) above is a divalent group represented by the formula:

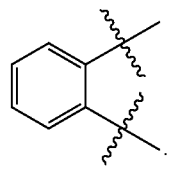

Item 7. A catalyst comprising an iron compound and a bisphosphine compound represented by Formula (4):

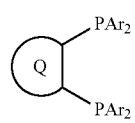  (4)

wherein Q is a divalent group derived from an optionally substituted aromatic or heteroaromatic ring by removing two hydrogen (H) atoms on adjacent carbon atoms; and each Ar is independently an optionally substituted aryl or heteroaryl group.

Item 8. The catalyst according to Item 7, wherein each Ar in Formula (4) above is a group represented by the formula:

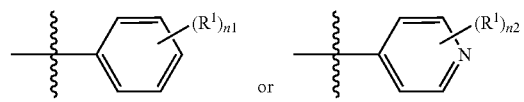

wherein each $R^1$ is independently H, F, an alkyl, alkoxy, aryl, aralkyl, trialkylsilyl, dialkylarylsilyl, alkyldiarylsilyl, or triarylsilyl group; n1 is an integer of 1 to 5; and n2 is an integer of 1 to 4.

Item 9. The catalyst according to Item 7, wherein each Ar in Formula (4) above is a group represented by the formula:

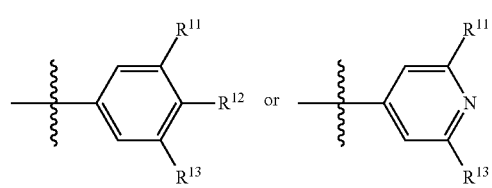

wherein $R^{11}$, $R^{12}$, and $R^{13}$ are each independently H, a $C_1$-$C_6$ alkyl, $C_1$-$C_6$ alkoxy, or trialkylsilyl group, with the proviso that not all of $R^{11}$, $R^{12}$, and $R^{13}$ are H.

Item 10. The catalyst according to Item 9, wherein each Ar in Formula (4) above is a group wherein $R^{12}$ is H; and $R^{11}$ and $R^{13}$ are each independently a $C_1$-$C_6$ alkyl, or trialkylsilyl group.

Item 11. The catalyst according to any one of Items 7 to 10, wherein Q in Formula (4) above is a divalent group represented by the formula:

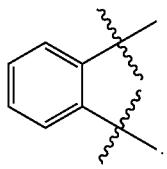

Item 12. A complex represented by Formula (5):

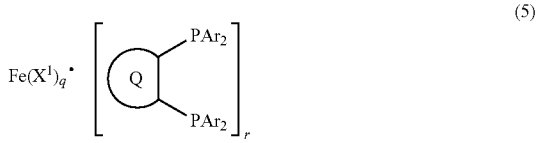

wherein $X^1$ is a halogen atom; q is an integer of 1, 2, or 3; r is an integer of 1 or 2; Q is a divalent group derived from an optionally substituted aromatic or heteroaromatic ring by removing two hydrogen (H) atoms on adjacent carbon atoms; and each Ar is independently an optionally substituted aryl or heteroaryl group.

Item 13. A bisphosphine compound represented by Formula (4a):

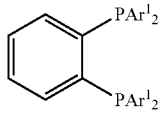

wherein each $Ar^1$ is independently a group represented by the formula:

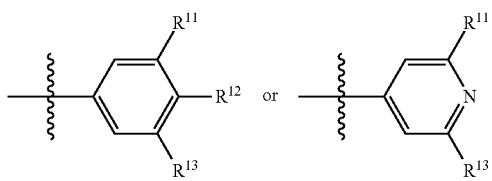

wherein $R^{11}$, $R^{12}$, and $R^{13}$ are each independently H, a $C_1$-$C_6$ alkyl, $C_1$-$C_6$ alkoxy, or trialkylsilyl group, with the proviso that not all of $R^{11}$, $R^{12}$, and $R^{13}$ are H; and with the proviso that two of $R^{11}$, $R^{12}$, and $R^{13}$ on the benzene ring are not H, and that the remaining one is not a methyl, ethyl, or propyl group.

Item 14. A process for producing a bisphosphine compound represented by Formula (4):

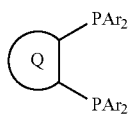

wherein Q is a divalent group derived from an optionally substituted aromatic or heteroaromatic ring by removing two hydrogen (H) atoms on adjacent carbon atoms; and each Ar is independently an optionally substituted aryl or heteroaryl group;

the process comprising:
reacting a compound represented by Formula (6):

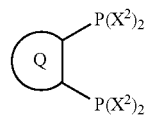

wherein each $X^2$ is a halogen atom, and Q is as defined above, with a metal reagent represented by Formula (7):

Ar-M  (7)

wherein M is Li or a group represented by the formula: $MgY^1$, with $Y^1$ being a halogen atom, and Ar is as defined above.

Item 15. The process according to Item 14, wherein Q in each of Formulae (4) and (6) is a group represented by the formula:

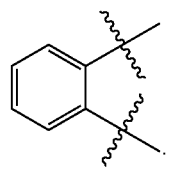 [SMILES: *c1ccccc1*]

Furthermore, as a result of extensive research in view of the above-mentioned object, the present inventors found that the object can be achieved by subjecting an alkyl halide and an aromatic zinc reagent, aromatic boron reagent, or aromatic aluminum reagent to a cross-coupling reaction, in the presence of iron (III) chloride and a bulky bisphosphine compound such as 1,2-bis(3,5-di-tert-butylphenyl)phosphino)benzene. The inventors conducted further research based on this finding, and consequently accomplished the invention. This invention is hereinafter denoted as a "second embodiment".

In summary, the present invention provides, among others, a process for producing an alkylated aromatic compound, as given below.

Item 16. A process for producing an aromatic compound represented by Formula (8):

R—Ar"  (8)

wherein R is an optionally substituted hydrocarbon group, and may have a group represented by —O— between a carbon-carbon bond of the hydrocarbon group; and Ar" is an optionally substituted aryl or heteroaryl group;

the process comprising:
reacting a compound represented by Formula (2):

R—X  (2)

wherein X is a halogen atom, and R is as defined above, with an organometallic reagent having a bond represented by Formula (9):

Ar"-Mtl  (9)

wherein Mtl is zinc (Zn), boron (B), or aluminum (Al), and Ar" is as defined above, in the presence of a catalyst for cross-coupling reactions comprising an iron compound and a bisphosphine compound represented by Formula (4a):

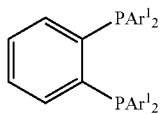
(4a)

wherein each $Ar^1$ is independently a group represented by the formula:

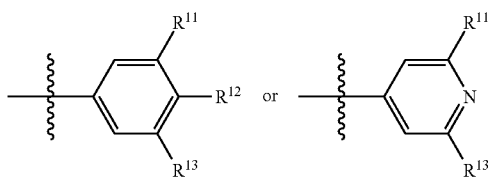

wherein $R^{11}$, $R^{12}$, and $R^{13}$ are each independently H, a $C_1$-$C_6$ alkyl, $C_1$-$C_6$ alkoxy, or trialkylsilyl group, with the proviso that not all of $R^{11}$, $R^{12}$, and $R^{13}$ are H.

Item 17. The process according to Item 16, wherein the bisphosphine compound represented by Formula (4a) is a group represented by Formula (4b):

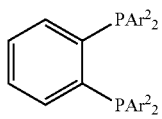
(4b)

wherein each $Ar^2$ is a group represented by the formula:

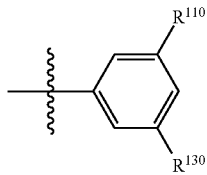

wherein $R^{110}$ and $R^{130}$ are each independently a $C_1$-$C_6$ alkyl, $C_1$-$C_6$ alkoxy, or tri($C_1$-$C_6$)alkylsilyl group.

Item 18. The process according to Item 16 or 17, wherein the iron compound is a divalent or trivalent iron salt, or a solvate thereof.

Item 19. The process according to Item 16, 17, or 18, wherein $R^{110}$ and $R^{130}$ are each independently tert-butyl or trimethylsilyl.

Effects of the Invention

The catalysts of the invention comprising an iron compound and a bisphosphine compound allow cross-coupling reactions between alkyl halides and aromatic magnesium reagents to efficiently proceed. Thus, the catalysts of the invention are useful for cross-coupling reactions. Using these catalysts, a variety of alkylated aromatic compounds (cross-coupling compounds) can be produced with high yield. The cross-coupling reactions are extremely useful in the synthesis of organic liquid crystal molecules, organic electronic materials, and pharmaceutical/agrochemical intermediates.

Among the catalysts of the invention, the use of a catalyst comprising a bisphosphine compound having bulky substituents on the phosphorus atoms allows a cross-coupling reaction to more efficiently proceed. In this case, not only a cross-coupling reaction that uses an aromatic magnesium reagent, but also a cross-coupling reaction that uses an aromatic zinc reagent, aromatic boron reagent, or aromatic aluminum reagent proceeds extremely efficiently.

BRIEF DESCRIPTION OF THE SEVERAL VIEWS OF THE DRAWINGS

FIG. 2 shows the crystal data of the complex produced in Example 1 (1) based on X-ray analysis.

FIG. 4 shows the crystal data of the complex produced in Example 1 (2) based on X-ray analysis.

DETAILED DESCRIPTION OF THE INVENTION

1. First Embodiment

Cross-Coupling Reactions Using Mg Reagent

Figure 1:
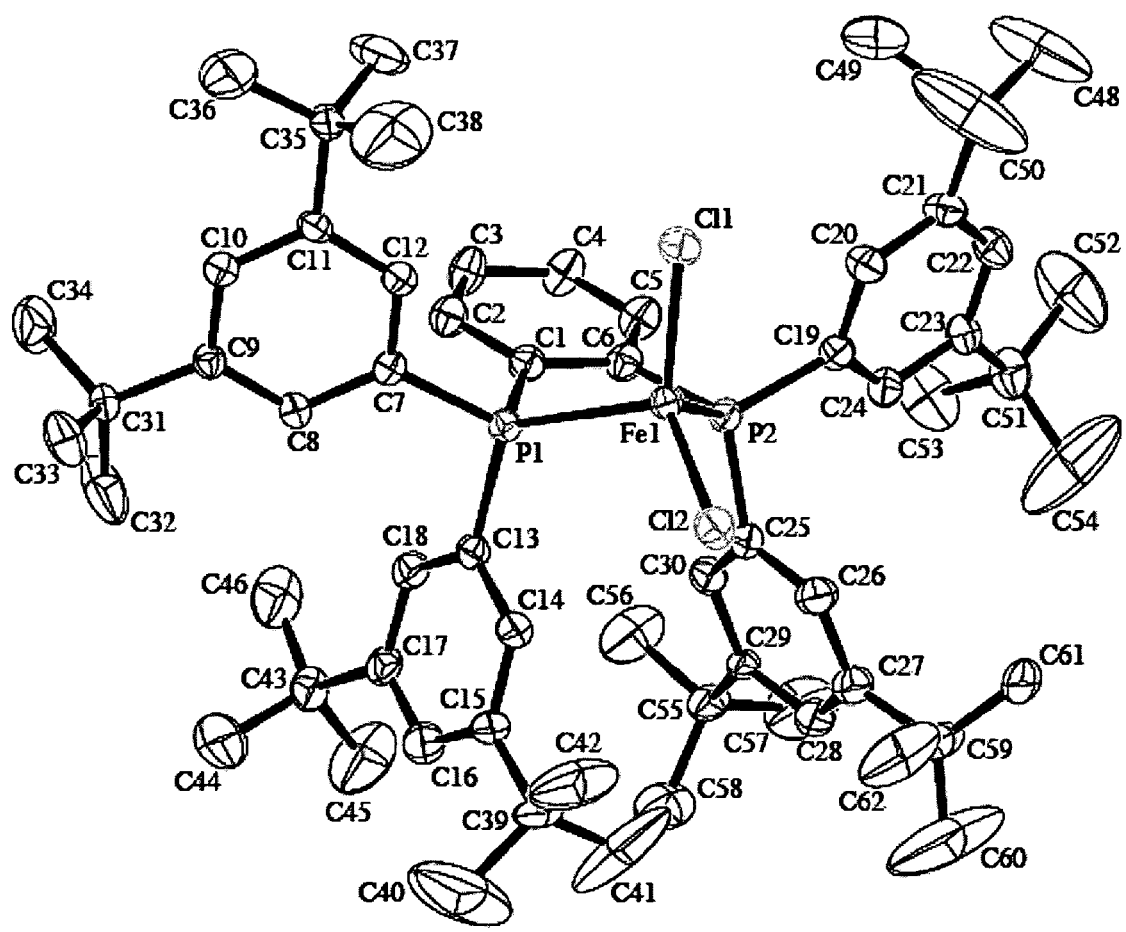
FIG. 1 shows the structure (ORTEP) of iron chloride.1,2-bis(bis(3,5-di-tert-butylphenyl)phosphino)benzene complex ($FeCl_2$.L) produced in Example 1 (1), as determined by X-ray analysis.

The present invention is directed to a process as shown by the following scheme for producing an aromatic compound represented by Formula (1). The process comprises reacting a compound represented by Formula (2) with a magnesium reagent represented by Formula (3), in the presence of a catalyst for cross-coupling reactions comprising an iron compound (or iron catalyst) and a bisphosphine compound represented by Formula (4).

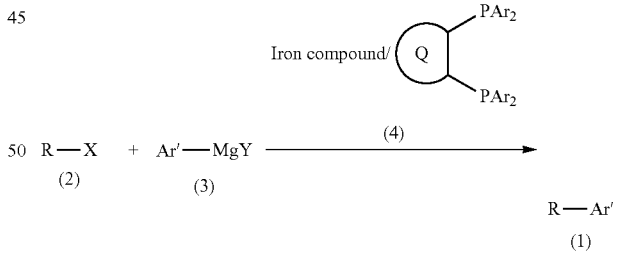

wherein R represents an optionally substituted hydrocarbon group, and may have a group represented by —O— between a carbon-carbon bond of the hydrocarbon group; X represents a halogen atom; Ar" represents an optionally substituted aryl or heteroaryl group; Y represents a halogen atom; Q represents a divalent group derived from an optionally substituted aromatic or heteroaromatic ring by removing two hydrogen (H) atoms on adjacent carbon atoms; and each Ar independently represents an optionally substituted aryl or heteroaryl group.

In the compounds represented by Formulae (1) and (2), R represents an optionally substituted hydrocarbon group, and may have a group represented by —O— between a carbon-carbon bond of the hydrocarbon group.

Examples of hydrocarbon groups include $C_1$-$C_{30}$ hydrocarbon groups, and polymeric hydrocarbon groups containing more carbon atoms. Such hydrocarbon groups may be saturated or unsaturated, and may be acyclic, cyclic, or in a form including both acyclic and cyclic structures. In the case of an unsaturated hydrocarbon group, the carbon atom that is attached to X (i.e., that forms a bond with Ar' via a cross-coupling reaction) is preferably a sp$^3$ hybridized carbon atom.

Examples of such hydrocarbon groups include $C_2$-$C_{30}$ alkyl, $C_3$-$C_{30}$ alkenyl, $C_3$-$C_{30}$ alkynyl, $C_5$-$C_{30}$ alkyldienyl, $C_7$-$C_{30}$ aralkyl, $C_3$-$C_{30}$ cycloalkyl, $C_3$-$C_{30}$ cycloalkenyl, and ($C_3$-$C_{15}$ cycloalkyl)$C_1$-$C_{15}$ alkyl groups.

The "$C_2$-$C_{30}$ alkyl" represented by R is preferably $C_2$-$C_{15}$ alkyl, and more preferably $C_4$-$C_{12}$ alkyl. Examples of alkyl groups include ethyl, propyl, isopropyl, n-butyl, sec-butyl, tert-butyl, isobutyl, pentyl, neopentyl, hexyl, heptyl, octyl, nonyl, decyl, dodecyl, and octadecyl.

The "$C_3$-$C_{30}$ alkenyl" represented by R is preferably $C_3$-$C_{15}$ alkenyl, and more preferably $C_4$-$C_{10}$ alkenyl. Examples of alkenyl groups include 2-propenyl, 2-methyl-2-propenyl, 2-methylallyl, 2-butenyl, 3-butenyl, and 4-pentenyl.

The "$C_3$-$C_{30}$ alkynyl" represented by R is preferably $C_3$-$C_{15}$ alkynyl, and more preferably $C_4$-$C_{10}$ alkynyl. Examples of alkynyl groups include 3-butynyl and 4-pentynyl.

The "$C_5$-$C_{30}$ alkyldienyl" represented by R is preferably $C_5$-$C_{15}$ alkyldienyl, and more preferably $C_6$-$C_{10}$ alkyldienyl. Examples of alkyldienyl groups include 3,5-hexadienyl and cyclopentadienyl.

The "$C_7$-$C_{30}$ aralkyl" represented by R is preferably $C_7$-$C_{12}$ aralkyl. Examples of aralkyl groups include benzyl, phenethyl, diphenylmethyl, triphenylmethyl, 1-naphthylmethyl, 2-naphthylmethyl, 2,2-diphenylethyl, 3-phenylpropyl, 4-phenylbutyl, 5-phenylpentyl, and 1,2,3,4-tetrahydronaphthyl. For example, 2,2-diphenylethyl, 3-phenylpropyl, 4-phenylbutyl, and 5-phenylpentyl are preferred.

The "$C_3$-$C_{30}$ cycloalkyl" represented by R is preferably $C_3$-$C_{10}$ cycloalkyl. Examples of cycloalkyl groups include cyclopropyl, cyclobutyl, cyclopentyl, cyclohexyl, cycloheptyl, bornyl, norbornyl, adamantyl, noradamantyl, norpinyl, and decahydronaphthyl.

The "$C_3$-$C_{30}$ cycloalkenyl" represented by R is preferably $C_3$-$C_{10}$ cycloalkenyl. Examples of cycloalkenyl groups include cyclopropenyl, cyclobutenyl, cyclopentenyl, cyclohexenyl, norbornenyl, and norbornadienyl.

The "($C_3$-$C_{15}$ cycloalkyl)$C_1$-$C_{15}$ alkyl" represented by R is preferably ($C_3$-$C_{10}$ cycloalkyl) $C_1$-$C_{10}$ alkyl. Specific examples include (cyclopropyl)$C_1$-$C_3$ alkyl, (cyclobutyl)$C_1$-$C_3$ alkyl, (cyclopentyl)$C_1$-$C_3$ alkyl, (cyclohexyl)$C_1$-$C_3$ alkyl, (cycloheptyl)$C_1$-$C_3$ alkyl, and (adamantyl)$C_1$-$C_3$ alkyl.

Further, R may have a group represented by —O— between a carbon-carbon bond of the hydrocarbon group represented by R described above. Specifically, the hydrocarbon group represented by R may contain one or more ether linkages.

The hydrocarbon group represented by R may have substituent(s). The substituent(s) are not particularly limited as long as they do not adversely affect the cross-coupling reaction. Examples of substituents include halogen atoms (e.g., F, Cl, and Br; in particular, F); alkoxy (e.g., $C_1$-$C_6$ alkoxy such as methoxy, ethoxy, propoxy, and butoxy); aryl (e.g., $C_6$-$C_{20}$ monocyclic or polycyclic aryl such as phenyl, toluoyl, naphthyl, biphenyl, and terphenyl); heteroaryl (e.g., $C_6$-$C_{20}$ monocyclic or polycyclic heteroaryl such as thienyl, furyl, imidazolyl, pyrazolyl, pyridyl, pyrazinyl, pyrimidinyl, pyridazinyl, indolyl, quinolyl, and isoquinolyl); aryloxy (e.g., groups represented by the formula: (the above-mentioned aryl)-O—); aralkyloxy (e.g., benzyloxy); esters (e.g., groups represented by the formula: —C(=O)OR$^2$, wherein R$^2$ is $C_1$-$C_{10}$ alkyl or the like);

dialkylamides (e.g., groups represented by the formula: —C(=O)N(R$^3$)$_2$, wherein R$^3$ is $C_1$-$C_{10}$ alkyl or the like); optionally protected hydroxy (e.g., groups represented by the formula: —OR$^4$, wherein R$^4$ is H, alkylcarbonyl, alkoxycarbonyl, aralkyl, trialkylsilyl, or the like); trialkylsilyl (e.g., trimethylsilyl, dimethyl-tert-butylsilyl, and triethylsilyl); and acetal (e.g., groups represented by the formula: —CR$^5$(OR$^6$)(OR$^7$), wherein R$^5$ is hydrogen or optionally substituted $C_1$-$C_6$ alkyl, and R$^6$ and R$^7$ are each independently alkyl (e.g., methyl, ethyl, propyl, isopropyl, n-butyl, sec-butyl, tert-butyl, pentyl, and hexyl) and may be cross-linked together to form divalent alkylene; examples of R$^6$ and R$^7$ include methyl and ethyl. When R$^6$ and R$^7$ are cross-linked together, examples of R$^6$ and R$^7$ include ethylene and trimethylene.

These substituents may be present at substitutable position(s) of the hydrocarbon group in a number of one or more, for example, 1 to 4, and more particularly, 1 to 3. When there are two or more substituents, these substituents may be the same or different from one another.

In the compounds represented by Formula (2), X represents halogen. Specifically, X is Cl, Br, I, or the like, and preferably Br.

In the compounds represented by each of Formulae (1) and (3), Ar' is optionally substituted aryl or heteroaryl.

Examples of aryl groups for the optionally substituted aryl represented by Ar' include mono- to pentacyclic aryl. Specific examples include phenyl, toluoyl, naphthyl, anthryl, phenanthryl, fluorenyl, tetracenyl, and pentacenyl.

Examples of heteroaryl groups for the optionally substituted heteroaryl represented by Ar' include mono- to tetracyclic heteroaryl having at least one hetero atom selected from oxygen, nitrogen, and sulfur on their rings. Specific examples include thienyl, furyl, imidazolyl, pyrazolyl, pyridyl, pyrazinyl, pyrimidinyl, pyridazinyl, indolyl, quinolyl, and isoquinolyl.

These aryl or heteroaryl groups may have substituent(s); the substituent(s) are not particularly limited as long as they do not adversely affect the cross-coupling reaction of the invention.

Examples of substituents include halogen atoms (e.g., F, Cl, and Br; in particular, F); alkoxy (e.g., $C_1$-$C_6$ alkoxy such as methoxy, ethoxy, propoxy, and butoxy); aryl (e.g., $C_6$-$C_{20}$ monocyclic or polycyclic aryl such as phenyl, toluoyl, naphthyl, biphenyl, and terphenyl); aryloxy (e.g., groups represented by the formula: (the above-mentioned aryl)-O—); aralkyloxy (e.g., benzyloxy); esters (e.g., groups represented by the formula: —C(=O)OR$^{20}$, wherein R$^{20}$ is $C_1$-$C_{10}$ alkyl or the like); dialkylamides (e.g., groups represented by the formula: —C(=O)N(R$^{30}$)$_2$, wherein R$^{30}$ is $C_1$-$C_{10}$ alkyl or the like); optionally protected hydroxy (e.g., groups represented by the formula: —OR$^{40}$, wherein R$^{40}$ is H, alkylcarbonyl, alkoxycarbonyl, aralkyl, trialkylsilyl, or the like); trialkylsilyl (e.g., trimethylsilyl, dimethyl-tert-butylsilyl, and triethylsilyl); and acetal (e.g., groups represented by the formula: —CR$^{50}$(OR$^{60}$)(OR$^{70}$), wherein R$^{50}$ is hydrogen or optionally substituted $C_1$-$C_6$ alkyl, and R$^{60}$ and R$^{70}$ are each independently alkyl (e.g., methyl, ethyl, propyl, isopropyl, n-butyl, sec-butyl, tert-butyl, pentyl, and hexyl) and may be cross-linked together to form divalent alkylene; examples of R$^{60}$ and R$^{70}$ include methyl and ethyl.

When $R^{60}$ and $R^{70}$ are cross-linked together, examples of $R^{60}$ and $R^{70}$ include ethylene and trimethylene.

These substituents may be present at substitutable position(s) of the aryl or heteroaryl group in a number of one or more, for example, 1 to 4, and more particularly, 1 to 3. When there are two or more substituents, these substituents may be the same or different from one another.

In the compounds represented by Formula (3), Y represents halogen. Specifically, Y is F, Cl, Br, I, or the like; preferably Cl, Br, or I; and more preferably Br.

The iron compound is a divalent or trivalent iron salt or iron complex, and preferably a trivalent iron salt. These iron salts or iron complexes may also be solvates (e.g., hydrates) thereof. Specifically, the iron compound is preferably an iron (II) halide ($FeX^1_2$: $X^1$ is a halogen atom, and in particular, Cl), an iron (III) halide ($FeX^1_3$: $X^1$ is a halogen atom, and in particular, Cl), or a hydrate thereof. Particularly preferred are iron (III) chloride ($FeCl_3$), iron (III) chloride·hexahydrate ($FeCl_3 \cdot 6H_2O$), iron (II) chloride·tetrahydrate ($FeCl_2 \cdot 4H_2O$), and the like.

The bisphosphine compound represented by Formula (4) acts as the ligand of the iron compound, and promotes the cross-coupling reaction. In Formula (4), Q is a divalent group derived from an optionally substituted aromatic or heteroaromatic ring by removing two hydrogen (H) atoms on adjacent carbon atoms.

Examples of aromatic rings include $C_6$-$C_{20}$ monocyclic or polycyclic aromatic rings such as benzene, naphthalene, anthracene, and phenanthrene. Examples of divalent groups derived from such aromatic rings by removing two hydrogen (H) atoms on adjacent carbon atoms include those represented by the formulae:

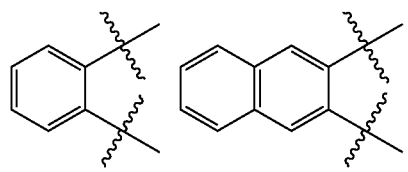

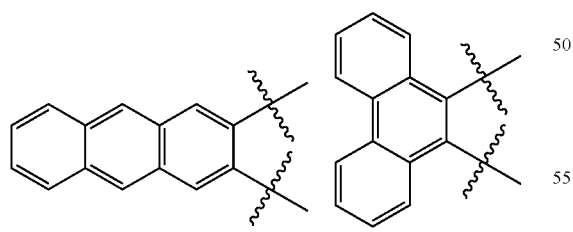

Examples of heteroaromatic rings include $C_4$-$C_{20}$ monocyclic or polycyclic heteroaromatic groups having a hetero atom selected from N, O, and S. Examples include thiophene, furan, imidazole, pyrazole, pyridine, pyrazine, pyrimidine, pyridazine, indole, quinoline, isoquinoline, phthalazine, naphthyridine, quinoxaline, quinazoline, and cinnoline. Examples of divalent groups derived from such heteroaromatic rings by removing two hydrogen (H) atoms on adjacent carbon atoms include those represented by the formulae:

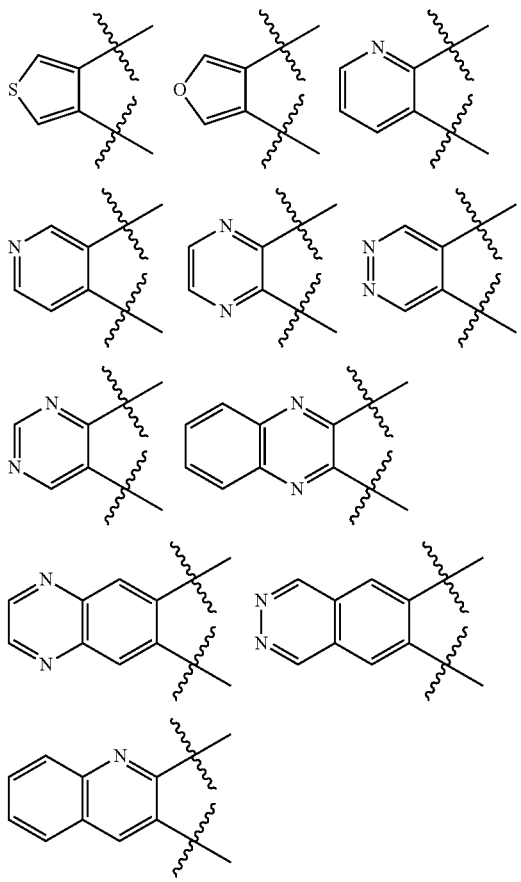

These aromatic and heteroaromatic rings may have substituent(s), for example, alkyl (e.g., $C_1$-$C_6$ alkyl such as methyl, ethyl, propyl, and butyl); and alkoxy (e.g., $C_1$-$C_6$ alkoxy such as methoxy, ethoxy, propoxy, and butoxy). The aromatic and heteroaromatic rings may have 1 to 3 substituents.

Preferred among such substituents is ortho-phenylene, i.e., a group represented by the formula:

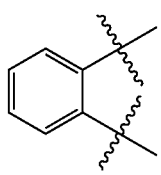 [SMILES: *c1ccccc1*]

In the bisphosphine compounds represented by Formula (4), each Ar is independently an optionally substituted aryl or heteroaryl group.

Examples of aryl groups for the optionally substituted aryl group represented by Ar include mono- to tetracyclic aryl such as phenyl, toluoyl, naphthyl, anthryl, phenanthryl, and fluorenyl. Phenyl is preferred.

Examples of heteroaryl groups for the optionally substituted heteroaryl group represented by Ar include $C_4$-$C_{20}$ monocyclic or polycyclic (in particular, mono- or bicyclic) heteroaryl groups having a hetero atom selected from N, O, and S. Examples include thiophene, furan, imidazole, pyrazole, pyridine, pyrazine, pyrimidine, pyridazine, indole, quinoline, isoquinoline, phthalazine, naphthyridine, quinoxaline, quinazoline, and cinnoline. Pyridyl is preferred; in particular, 4-pyridyl is preferred.

The aryl or heteroaryl may have substituent(s) at substitutable position(s) thereof. Examples of substituents include halogen atoms (e.g., F, Cl, and Br; in particular, F); alkyl (e.g., $C_1$-$C_6$ alkyl such as methyl, ethyl, n-propyl, isopropyl, and tert-butyl); alkoxy (e.g., $C_1$-$C_6$ alkoxy such as methoxy, ethoxy, propoxy, and butoxy); aryl (e.g., $C_6$-$C_{20}$ monocyclic or polycyclic aryl such as phenyl, toluoyl, 2,6-dimethylphenyl, and naphthyl); aralkyl (e.g., benzyl and phenethyl); aryloxy (e.g., groups represented by the formula: (the above-mentioned aryl)-O—); aralkyloxy (e.g., benzyloxy); trialkylsilyl (e.g., trimethylsilyl, dimethyl-tert-butylsilyl, and triethylsilyl); dialkylarylsilyl (e.g., dimethylphenylsilyl); alkyldiarylsilyl (e.g., tert-butyldiphenylsilyl); and triarylsilyl (e.g., triphenylsilyl).

Preferred examples of substituents include $C_1$-$C_6$ alkyl such as methyl, ethyl, n-propyl, isopropyl, and tert-butyl; $C_1$-$C_6$ alkoxy such as methoxy, ethoxy, propoxy, and butoxy; $C_6$-$C_{20}$ monocyclic or polycyclic aryl such as phenyl, toluoyl, 2,6-dimethylphenyl, and naphthyl; and trialkyl (in particular, tri-$C_1$-$C_6$ alkyl)silyl such as trimethylsilyl, dimethyl-tert-butylsilyl, and triethylsilyl.

These substituents may be present at substitutable position(s) of the aryl or heteroaryl group in a number of one or more, for example, 1 to 4, and more particularly, 1 to 3. When there are two or more substituents, these substituents may be the same or different from one another.

In the compounds represented by Formula (4), preferred examples of each Ar include groups represented by the formula:

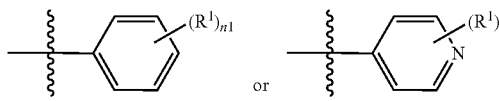

wherein each $R^1$ independently represents H, F, an alkyl, alkoxy, aryl, aralkyl, trialkylsilyl, dialkylarylsilyl, alkyldiarylsilyl, or triarylsilyl group; n1 represents an integer of 1 to 5; and n2 represents an integer of 1 to 4.

Substituents represented by $R^1$ can be specifically selected from those listed above. Preferred examples of substituents represented by $R^1$ include $C_1$-$C_6$ alkyl such as methyl, ethyl, n-propyl, isopropyl, and tert-butyl; $C_1$-$C_6$ alkoxy such as methoxy, ethoxy, propoxy, and butoxy; $C_6$-$C_{20}$ monocyclic or polycyclic aryl such as phenyl, toluoyl, 2,6-dimethylphenyl, and naphthyl; and trialkyl (in particular, tri-$C_1$-$C_6$ alkyl)silyl such as trimethylsilyl, dimethyl-tert-butylsilyl, and triethylsilyl. When n1 is an integer of 2 to 5, or n2 is an integer of 2 to 4, each $R^1$ may be the same or different. Advantageously, n1=2 or n2=2, and $R^1$ is $C_1$-$C_6$ alkyl (in particular, tert-butyl or isopropyl), or tri-$C_1$-$C_6$ alkylsilyl (in particular, trimethylsilyl). More advantageously, n1=1, and $R^1$ is $C_1$-$C_6$ alkoxy. Preferably, n1 is an integer of 1 to 3, and more preferably 1 or 2. Preferably, n2 is an integer of 1 to 3, and more preferably 2.

More preferred examples of each Ar include groups represented by the formula:

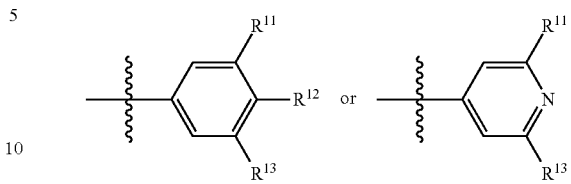

wherein $R^{11}$, $R^{12}$, and $R^{13}$ are each independently H, a $C_1$-$C_6$ alkyl, $C_1$-$C_6$ alkoxy, or trialkylsilyl group, with the proviso that not all of $R^{11}$, $R^{12}$, and $R^{13}$ are H.

Substituents represented by $R^{11}$, $R^{12}$, and $R^{13}$ can be specifically selected from those listed above. Preferred examples of substituents represented by $R^{11}$, $R^{12}$, and $R^{13}$ include $C_1$-$C_6$ such as methyl, ethyl, n-propyl, isopropyl, and tert-butyl; $C_1$-$C_6$ alkoxy such as methoxy, ethoxy, propoxy, and butoxy; and trialkyl (in particular, tri-$C_1$-$C_6$ alkyl)silyl such as trimethylsilyl, dimethyl-tert-butylsilyl, and triethylsilyl. Particularly preferably, $R^{12}$ is H, and each of $R^{11}$ and $R^{13}$ is $C_1$-$C_6$ alkyl (in particular, tert-butyl) or tri-$C_1$-$C_6$ alkylsilyl (in particular, trimethylsilyl). Alternatively, $R^{12}$ is $C_1$-$C_6$ alkoxy, and each of $R^{11}$ and $R^{13}$ is H.

Other more preferred examples of each Ar include groups represented by the formula:

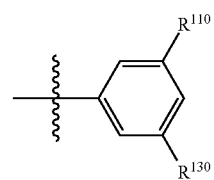

wherein $R^{110}$ and $R^{130}$ are each independently a $C_3$-$C_6$ alkyl, $C_1$-$C_6$ alkoxy, or tri($C_1$-$C_6$)alkylsilyl group.

Examples of $C_3$-$C_6$ alkyl include n-propyl, isopropyl, and tert-butyl; examples of $C_1$-$C_6$ alkoxy include methoxy, ethoxy, propoxy, and butoxy; and examples of tri($C_1$-$C_6$) alkylsilyl include trimethylsilyl and triethylsilyl. Each of $R^{110}$ and $R^{130}$ is preferably tert-butyl or trimethylsilyl.

Still more preferred examples of each Ar include groups represented by the formula:

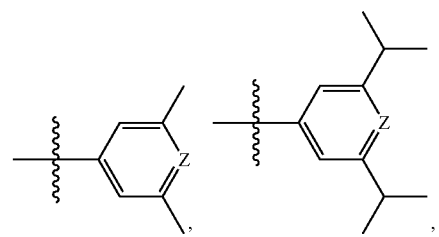

wherein Z represents —CH= or —N=; advantageously, Z is —CH=.

Particularly preferably, each Ar is a group represented by the formula:

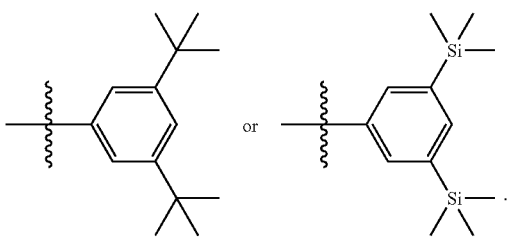 [SMILES: *c1cc(C(C)(C)C)cc(C(C)(C)C)c1 ; *c1cc([Si](C)(C)C)cc([Si](C)(C)C)c1]

Among the bisphosphine compounds represented by Formula (4), preferred bisphosphine compounds include those represented by the formula:

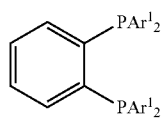

(4a)

wherein each $Ar^1$ independently represents a group represented by the formula:

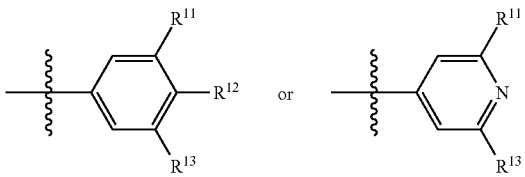

wherein $R^{11}$, $R^{12}$, and $R^{13}$ are as defined above.

The bisphosphine compounds represented by Formula (4a) have phenyl groups having bulky substituents on the phosphorus atoms, and, therefore, have a high effect of promoting cross-coupling reactions.

Among the bisphosphine compounds represented by Formula (4), more preferred bisphosphine compounds include those represented by Formula (4b):

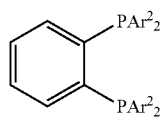

(4b)

wherein each $Ar^2$ represents a group represented by the formula:

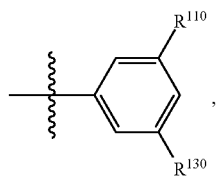

and $R^{110}$ and $R^{130}$ are as defined above.

The bisphosphine compounds represented by Formula (4b) above have, on the phosphorus atoms, phenyl groups having bulky groups in the meta position, and, therefore, have an extremely high effect of promoting cross-coupling reactions. Thus, cross-coupling reactions proceed with smaller catalytic amounts, allowing cross-coupling compounds to be produced with an extremely high yield.

According to the process of the invention for producing an aromatic compound represented by Formula (1), a compound represented by Formula (2) is reacted with a magnesium reagent represented by Formula (3), in the presence of a catalyst (a catalyst for cross-coupling reactions) comprising an iron compound and a bisphosphine compound represented by Formula (4), thereby producing the aromatic compound represented by Formula (1).

Reaction solvents are not particularly limited as long as they do not adversely affect the reaction of the invention. Examples of reaction solvents include ether solvents such as diethylether, diisopropylether, dibutylether, tert-butyl methyl ether, cyclopentyl methyl ether, tetrahydrofuran (THF), 1,4-dioxane, and dimethoxyethane; aromatic hydrocarbon solvents such as benzene, toluene, and xylene; aliphatic hydrocarbon solvents such as pentane and hexane; and mixtures thereof. Tetrahydrofuran is preferred.

In the reaction of the invention, the concentration of the compound represented by Formula (2) in the reaction solvent can typically be adjusted to about 0.1 to 2.0 mol/L, preferably about 0.2 to 1.5 mol/L, and more preferably about 0.5 to 1.0 mol/L.

The amount of the magnesium reagent represented by Formula (3) is typically 1 to 3 mol, preferably 1 to 2 mol, and more preferably 1.1 to 1.5 mol, per mole of the compound represented by Formula (2). The process of the invention is efficient because the magnesium reagent represented by Formula (3) may be used in a stoichiometric amount with respect to the compound represented by Formula (2). The process of the invention is advantageous over a process using a zinc reagent as disclosed in Non-Patent Document 8, which results

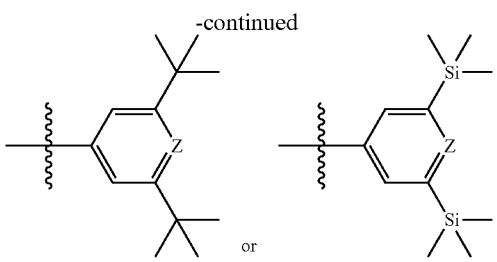

in the waste of one equivalent of an aromatic group that is involved in a cross-coupling reaction.

The amount of the iron compound is 0.1 to 5 mol %, preferably 0.1 to 3 mol %, and more preferably 0.5 to 3 mol %, per mole of the compound represented by Formula (2).

The amount of the bisphosphine compound represented by Formula (4) is typically 0.1 to 10 mol %, preferably 0.2 to 6 mol %, and more preferably 0.5 to 3 mol %, per mole of the compound represented by Formula (2). The molar ratio of the iron compound to the bisphosphine compound represented by Formula (4) can typically be selected from the range of 1:1 to 1:3, and preferably 1:1 to 1:2. Within this range, the cross-coupling reaction proceeds with a good yield, allowing the formation of by-products to be suppressed.

In particular, the cross-coupling reaction is significantly promoted when using, as a ligand, a bulky bisphosphine compound represented by Formula (4b) described below. Therefore, the amounts of the iron compound and bisphosphine compound can be reduced. For example, the amount of the iron compound may be 0.1 to 5.0 mol %, and preferably 0.5 to 3 mol %, per mole of the compound represented by Formula (2), and the amount of the bisphosphine compound may be 0.1 to 10.0 mol %, and preferably 0.5 to 6 mol %, per mole of the compound represented by Formula (2).

A typical reaction procedure of the process of the invention for producing an aromatic compound represented by Formula (1) is preferably performed by a method wherein the magnesium reagent represented by Formula (3) is added (in particular, slowly added dropwise) to a solution containing the catalyst (the catalyst for cross-coupling reactions) comprising an iron compound and a bisphosphine compound represented by Formula (4), and containing the compound represented by Formula (2).

The catalyst for cross-coupling reactions can be prepared by mixing the iron compound with the bisphosphine compound represented by Formula (4) in the reaction system; isolation is not particularly necessary.

Alternatively, the catalyst may be prepared as follows: the iron compound is reacted with the bisphosphine compound represented by Formula (4) to form a complex (catalyst for cross-coupling reactions), which is further isolated, and the isolated product is subjected to the cross-coupling reaction. The complex (catalyst for cross-coupling reactions) can typically be prepared by reacting the iron compound and the bisphosphine compound represented by Formula (4) in a molar ratio of, for example, 1:1 to 1:2, at 30 to 80° C. in a solvent (e.g., an alcohol solvent such as ethanol). An exemplary scheme for producing a catalyst for cross-coupling reactions represented by Formula (5) from an iron halide and a bisphosphine compound represented by Formula (4) is shown below:

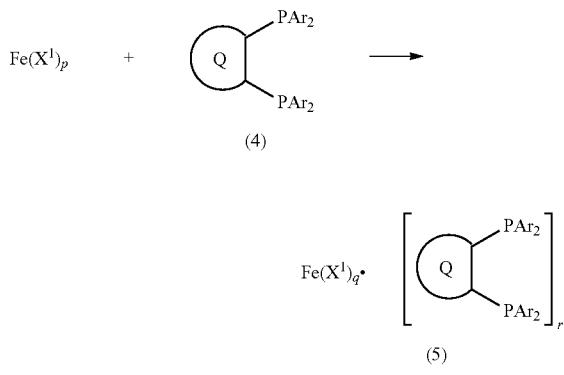

wherein $X^1$ represents a halogen atom, and in particular, Cl; p is 2 or 3, and in particular, 2; q is 1, 2, or 3, and in particular, 2; r is 1 or 2, and in particular, 1; and Q and each Ar are as defined above.

Examples of typical complexes (catalysts for cross-coupling reactions) include $FeCl_1.L$, $FeCl_2.L$, $FeCl_2.L_2$, and $FeCl_3.L$, wherein L represents a bisphosphine compound represented by Formula (4). $FeCl_2.L$ is preferred.

In the case of a cross-coupling reaction using an isolated complex (a catalyst for cross-coupling reactions), the amount of the complex may typically be 0.1 to 5 mol %, preferably 0.1 to 3 mol %, and more preferably 0.5 to 3 mol %, per mole of the compound represented by Formula (2). The reaction advantageously proceeds even when using the complex alone; however, the bisphosphine compound represented by Formula (4) may be added as needed. This may allow the formation of byproducts, such as olefins, to be suppressed. In this case, the amount of the bisphosphine compound represented by Formula (4) that is to be added may be adjusted such that the molar ratio of the iron compound to the bisphosphine compound represented by Formula (4) in the reaction system is typically in the range of 1:1 to 1:3, and preferably 1:1 to 1:2, as described above.

The magnesium reagent represented by Formula (3) can be prepared from magnesium (Mg) and a corresponding compound represented by Formula (3'):

$$Ar'—Y \quad (3')$$

wherein Ar' and Y are as defined above, according to a known method (see, e.g., *The Fifth Series of Experimental Chemistry*, vol. 18, pp. 59-76, etc.).

Examples of solvents include ether solvents such as diethylether, diisopropylether, dibutylether, tert-butyl methyl ether, cyclopentyl methyl ether, tetrahydrofuran (THF), 1,4-dioxane, and dimethoxyethane; aromatic hydrocarbon solvents such as benzene, toluene, and xylene; and mixtures thereof. Tetrahydrofuran (THF) is preferred. The concentration of a solution of the magnesium reagent may typically be about 0.5 to 1.5 mol/L.

In the invention, in order to suppress the homocoupling between molecules of the magnesium reagent represented by Formula (3), or suppress the formation of by-products such as olefins, to thereby enhance the yield of the target cross-coupling reaction product represented by Formula (1), it is advantageous to slowly add the magnesium reagent represented by Formula (3) dropwise to a solution containing the catalyst for cross-coupling reactions and the compound represented by Formula (2). The rate of the dropwise addition will depend upon the reaction scale; however, for example, when the amount of the compound represented by Formula (2) in the reaction system is about 100 to 1000 mmol, the solution of the magnesium reagent represented by Formula (3) is preferably added at a rate of about 0.5 to 50 mmol/min; and when the amount of the compound represented by Formula (2) in the reaction system is about 1 to 100 mmol, the solution of the magnesium reagent represented by Formula (3) is preferably added at a rate of about 0.005 to 5 mmol/min.

Typically, the reaction is preferably conducted under anhydrous conditions in an inert gas (e.g., argon or nitrogen) atmosphere. The reaction temperature is typically −10 to 80° C., preferably 0 to 60° C., and more preferably 20 to 60° C. The reaction pressure is not particularly limited; typically, atmospheric pressure is used.

After the reaction has been conducted as above, the reaction mixture is quenched with a protonic solvent (e.g., water, ammonium chloride solution, or dilute hydrochloric acid) and extracted; if necessary, the extract is subjected to a purification procedure such as column chromatography, distillation, recrystallization, trituration, or the like, thereby giving the target compound represented by Formula (1).

2. Second Embodiment

Cross-Coupling Reactions Using Zn, B, or Al Reagent

The present invention is directed to a process as shown by the following scheme for producing an aromatic compound represented by Formula (8). The process comprises reacting a compound represented by Formula (2) with an organometallic reagent having a bond represented by Formula (9), in the presence of a catalyst for cross-coupling reactions comprising an iron compound and a bisphosphine compound represented by Formula (4a).

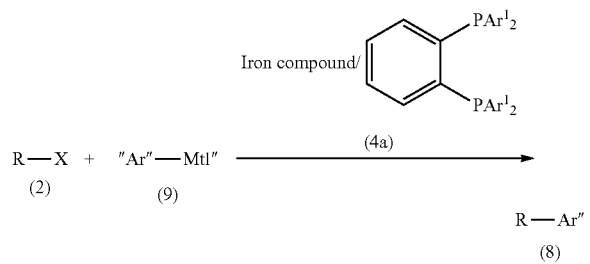

R—Ar" (8)

wherein Ar" is an optionally substituted aryl or heteroaryl group; Mtl represents zinc (Zn), boron (B), or aluminum (Al); and R, X, and each $Ar^1$ are as defined above.

In the compounds represented by Formulae (2) and (8), R represents an optionally substituted hydrocarbon group, and may have a group represented by —O— between a carbon-carbon bond of the hydrocarbon group. X represents a halogen atom. That is, R and X are synonymous with the R and X described in the "1. First Embodiment" section.

In the compounds represented by Formulae (8) and (9), Ar" is an optionally substituted aryl or heteroaryl group. That is, Ar" is synonymous with the Ar' described in the "1. First Embodiment" section.

Examples of organometallic reagents represented by Formula (9) include an organozinc reagent, an organoboron reagent, and an organoaluminum reagent. Specific examples of these reagents are given below.

Organozinc reagents are not particularly limited as long as they have, for example, an Ar"—Zn bond. The organometallic reagent can be selected from, for example, the following reagents:

(Ar")$_2$Zn          (9a)

(Ar")$_2$Zn.2MgX'$_2$          (9b)

Ar"ZnX'.MgX'$_2$          (9c)

wherein X' represents a halogen atom; when two X's are included, each X' may be the same or different; and Ar" is as defined above; when two Ar"s are included, each Ar" may be the same or different.

These reagents can be readily prepared in accordance with the teachings of, for example: 1) M. Schlosser ed. "Organometallics in Synthesis, A Manual" second edition, Wiley, Weinheim, 2002; 2) P. Knochel, P. Jones, Organozinc Reagents, Oxford University Press, New York, 1999; and 3) E. Erdik, Organozinc Reagents in Organic Synthesis, CRC Press, New York, 1996.

Organoboron reagents are not particularly limited as long as they have, for example, an Ar"—B bond. The organoboron reagent can be selected from, for example, the following reagents:

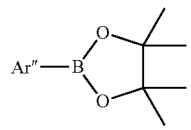

(9d)

(Ar")$_k$B(OR$^8$)$_{3-k}$          (9e)

wherein $R^8$ represents $C_1$-$C_6$ alkyl; k represents 1, 2, or 3; and Ar" is as defined above.

These reagents can be readily prepared in accordance with the teachings of, for example, M. Schlosser ed. "Organometallics in Synthesis, A Manual" second edition, Wiley, Weinheim, 2002.

Organoaluminum reagents are not particularly limited as long as they have, for example, an Ar"—Al bond. The organoaluminum reagent can be selected from, for example, the following reagents:

(Ar")$_m$Al(R$^9$)$_{3-m}$          (9f)

(Ar")$_m$Al(R$^9$)$_{3-m}$·MgX'$_2$          (9g)

wherein $R^9$ represents $C_1$-$C_6$ alkyl; X' represents a halogen atom; m represents 1, 2, or 3; and Ar" is as defined above.

These reagents can be readily prepared in accordance with the teachings of, for example, M. Schlosser ed. "Organometallics in Synthesis, A Manual" second edition, Wiley, Weinheim, 2002.

The iron compound is a divalent or trivalent iron salt or iron complex, and preferably a trivalent iron salt. These iron salts or iron complexes may also be solvates (e.g., hydrates) thereof. Specifically, the iron compound is preferably an iron (II) halide (FeX$^1$$_2$: $X^1$ is a halogen atom, and in particular, Cl), an iron (III) halide (FeX$^1$$_3$: $X^1$ is a halogen atom, and in particular, Cl), or a hydrate thereof. Particularly preferred are iron (III) chloride (FeCl$_3$), iron (III) chloride.hexahydrate (FeCl$_3$.6H$_2$O), iron (II) chloride.tetrahydrate (FeCl$_2$.4H$_2$O), and the like.

Suitable examples of the bisphosphine compounds represented by Formula (4a) include bisphosphine compounds represented by Formula (4b). Because of the presence of bulky groups in the meta position, the bisphosphine compounds represented by Formula (4b) have an extremely high effect of promoting cross-coupling reactions. For example, the reaction yield for cross-coupling reactions using the compounds represented by Formula (4b) is extremely high, compared to the yield for cross-coupling reactions using 1,2-bis (diphenylphosphino)benzene. See, for example, Examples 5, 6, 10, 11, and 12.

According to the process of the invention for producing an aromatic compound represented by Formula (8), a compound represented by Formula (2) is reacted with an organometallic reagent having a bond represented by Formula (9), in the presence of a catalyst (a catalyst for cross-coupling reactions) comprising an iron compound and a bisphosphine compound represented by Formula (4a), thereby producing the aromatic compound represented by Formula (8).

A specific coupling reaction using each of an organozinc reagent, an organoboron reagent, and an organoaluminum reagent as the organometallic reagent having a bond represented by Formula (9) is now described.

A typical example of a coupling reaction using an organozinc reagent is described hereinafter. A compound represented by Formula (2) is reacted with an organozinc reagent prepared according to any of the above-mentioned various known methods, in the presence of a catalyst (a catalyst for cross-coupling reactions) comprising an iron compound and a bisphosphine compound represented by Formula (4a), thereby producing an aromatic compound represented by Formula (8).

Reaction solvents are not particularly limited as long as they do not adversely affect the reaction of the invention. Examples of reaction solvents include ether solvents such as diethylether, diisopropylether, dibutylether, tert-butyl methyl ether, cyclopentyl methyl ether, tetrahydrofuran (THF), 1,4-dioxane, and dimethoxyethane; aromatic hydrocarbon solvents such as benzene, toluene, and xylene; aliphatic hydrocarbon solvents such as pentane and hexane; and mixtures thereof. Tetrahydrofuran is preferred.

In the reaction of the invention, the concentration of the compound represented by Formula (2) in the reaction solvent can typically be adjusted to about 0.1 to 2.0 mol/L, preferably about 0.2 to 1.5 mol/L, and more preferably about 0.5 to 1.0 mol/L.

The amount of the organozinc reagent calculated as the number of moles of zinc atoms is typically 1 to 3 mol, preferably 1 to 2 mol, and more preferably 1.1 to 1.5 mol, per mole of the compound represented by Formula (2).

The amount of the iron compound is 0.1 to 5 mol %, preferably 0.1 to 3 mol %, and more preferably 0.5 to 3 mol %, per mole of the compound represented by Formula (2).

The amount of the bisphosphine compound represented by Formula (4a) is typically 0.1 to 10 mol %, preferably 0.2 to 6 mol %, and more preferably 0.5 to 3 mol %, per mole of the compound represented by Formula (2). The molar ratio of the iron compound to the bisphosphine compound represented by Formula (4a) can typically be selected from the range of 1:1 to 1:3, and preferably 1:1 to 1:2.

A typical reaction procedure of the process of the invention for producing an aromatic compound represented by Formula (8) is preferably performed by a method wherein the bisphosphine compound represented by Formula (4a), the iron compound, and the compound represented by Formula (2) are added to the organozinc reagent.

The catalyst for cross-coupling reactions can be prepared by mixing the iron compound with the bisphosphine compound represented by Formula (4a) in the reaction system. Alternatively, a complex between the iron compound and the bisphosphine compound may be formed before subjecting the resulting complex to the reaction. Such complexes can be formed, for example, referring to the scheme for producing the complex represented by Formula (5).

Typically, the reaction is preferably conducted under anhydrous conditions in an inert gas (e.g., argon or nitrogen) atmosphere. The reaction temperature is typically −10 to 80° C., preferably 0 to 60° C., and more preferably 20 to 60° C. The reaction pressure is not particularly limited; typically, atmospheric pressure is used.

After the reaction has been conducted as above, the reaction mixture is quenched with a protonic solvent (e.g., water, ammonium chloride solution, or dilute hydrochloric acid) and extracted; if necessary, the extract is subjected to a purification procedure such as column chromatography, distillation, recrystallization, trituration, or the like, thereby giving the target compound represented by Formula (8).

A typical example of a coupling reaction using an organoboron reagent is described hereinafter. A compound represented by Formula (2) is reacted with an organoboron reagent prepared according to any of the above-mentioned various known methods (or optionally, an organoboron ate complex obtained by activation) in the presence of a catalyst (a catalyst for cross-coupling reactions) comprising an iron compound and a bisphosphine compound represented by Formula (4a), thereby producing an aromatic compound represented by Formula (8).

Reaction solvents are not particularly limited as long as they do not adversely affect the reaction of the invention. Examples of reaction solvents include ether solvents such as diethylether, diisopropylether, dibutylether, tert-butyl methyl ether, cyclopentyl methyl ether, tetrahydrofuran (THF), 1,4-dioxane, and dimethoxyethane; aromatic hydrocarbon solvents such as benzene, toluene, and xylene; aliphatic hydrocarbon solvents such as pentane and hexane; and mixtures thereof. Tetrahydrofuran is preferred.

In the reaction of the invention, the concentration of the compound represented by Formula (2) in the reaction solvent can typically be adjusted to about 0.1 to 2.0 mol/L, preferably about 0.2 to 1.5 mol/L, and more preferably about 0.5 to 1.0 mol/L.

The amount of the organoboron reagent calculated as the number of moles of boron atoms is typically 1 to 3 mol, preferably 1 to 2 mol, and more preferably 1.1 to 1.5 mol, per mole of the compound represented by Formula (2).

The amount of the iron compound is 0.1 to 5 mol %, preferably 0.1 to 3 mol %, and more preferably 0.5 to 3 mol %, per mole of the compound represented by Formula (2).

The amount of the bisphosphine compound represented by Formula (4a) is typically 0.1 to 10 mol %, preferably 0.2 to 6 mol %, and more preferably 0.5 to 3 mol %, per mole of the compound represented by Formula (2). The molar ratio of the iron compound to the bisphosphine compound represented by Formula (4a) can typically be selected from the range of 1:1 to 1:3, and preferably 1:1 to 1:2.

A typical reaction procedure of the process of the invention for producing an aromatic compound represented by Formula (8) is preferably performed by a method wherein the bisphosphine compound represented by Formula (4a), the iron compound, and the compound represented by Formula (2) are added to the organoboron reagent, or optionally, an organoboron ate complex obtained by reacting the organoboron reagent with a nucleophilic agent capable of forming an ate complex via the nucleophilic reaction with the boron atom (e.g., n-butyllithium or tert-butyllithium). Such an organoboron ate complex is prepared by, for example, adding a nucleophilic agent such as tert-butyllithium or the like, and optionally a magnesium halide ($MgX^3_2$; $X^3$ represents a halogen atom, and in particular, Cl or F), to an organoboron reagent represented by Formula (9d) or (9e) above. The amount of the nucleophilic agent is typically about 1 to 1.5 mol per mole of the organoboron reagent. The amount of the magnesium halide is typically about 0.1 to 1.5 mol per mole of the organoboron reagent.

The catalyst for cross-coupling reactions can be prepared by mixing the iron compound with the bisphosphine compound represented by Formula (4a) in the reaction system. Alternatively, a complex between the iron compound and the bisphosphine compound may be formed before subjecting the resulting complex to the reaction. Such complexes can be formed, for example, referring to the scheme for producing the complex represented by Formula (5).

Typically, the reaction is preferably conducted under anhydrous conditions in an inert gas (e.g., argon or nitrogen)

atmosphere. The reaction temperature is typically −10 to 80° C., preferably 0 to 60° C., and more preferably 20 to 60° C. The reaction pressure is not particularly limited; typically, atmospheric pressure is used.

After the reaction has been conducted as above, the reaction mixture is quenched with a protonic solvent (e.g., water, ammonium chloride solution, or dilute hydrochloric acid) and extracted; if necessary, the extract is subjected to a purification procedure such as column chromatography, distillation, recrystallization, trituration, or the like, thereby giving the target compound represented by Formula (8).

A typical example of a coupling reaction using an organoaluminum reagent is described hereinafter. A compound represented by Formula (2) is reacted with an organoaluminum reagent prepared according to any of the above-mentioned various known methods in the presence of a catalyst (a catalyst for cross-coupling reactions) comprising an iron compound and a bisphosphine compound represented by Formula (4a), thereby producing an aromatic compound represented by Formula (8).

Reaction solvents are not particularly limited as long as they do not adversely affect the reaction of the invention. Examples of reaction solvents include ether solvents such as diethylether, diisopropylether, dibutylether, tert-butyl methyl ether, cyclopentyl methyl ether, tetrahydrofuran (THF), 1,4-dioxane, and dimethoxyethane; aromatic hydrocarbon solvents such as benzene, toluene, and xylene; aliphatic hydrocarbon solvents such as pentane and hexane; and mixtures thereof. Tetrahydrofuran is preferred.

In the reaction of the invention, the concentration of the compound represented by Formula (2) in the reaction solvent can typically be adjusted to about 0.1 to 2.0 mol/L, preferably about 0.2 to 1.5 mol/L, and more preferably about 0.5 to 1.0 mol/L.

The amount of the organoaluminum reagent calculated as the number of moles of aluminum atoms is typically 1 to 3 mol, preferably 1 to 2 mol, and more preferably 1.1 to 1.5 mol, per mole of the compound represented by Formula (2).

The amount of the iron compound is 0.1 to 5 mol %, preferably 0.1 to 3 mol %, and more preferably 0.5 to 3 mol %, per mole of the compound represented by Formula (2).

The amount of the bisphosphine compound represented by Formula (4a) is typically 0.1 to 10 mol %, preferably 0.2 to 6 mol %, and more preferably 0.5 to 3 mol %, per mole of the compound represented by Formula (2). The molar ratio of the iron compound to the bisphosphine compound represented by Formula (4a) can typically be selected from the range of 1:1 to 1:3, and preferably 1:1 to 1:2.

A typical reaction procedure of the process of the invention for producing an aromatic compound represented by Formula (8) is preferably performed by a method wherein the bisphosphine compound represented by Formula (4a), the iron compound, and the compound represented by Formula (2) are added to the organoaluminum reagent.

The catalyst for cross-coupling reactions can be prepared by mixing the iron compound with the bisphosphine compound represented by Formula (4a) in the reaction system. Alternatively, a complex between the iron compound and the bisphosphine compound may be formed before subjecting the resulting complex to the reaction. Such complexes can be formed, for example, referring to the scheme for producing the complex represented by Formula (5).

Typically, the reaction is preferably conducted under anhydrous conditions in an inert gas (e.g., argon or nitrogen) atmosphere. The reaction temperature is typically −10 to 80° C., preferably 0 to 60° C., and more preferably 20 to 60° C. The reaction pressure is not particularly limited; typically, atmospheric pressure is used.

After the reaction has been conducted as above, the reaction mixture is quenched with a protonic solvent (e.g., water, ammonium chloride solution, or dilute hydrochloric acid) and extracted; if necessary, the extract is subjected to a purification procedure such as column chromatography, distillation, recrystallization, trituration, or the like, thereby giving the target compound represented by Formula (8).

3. Production of Bisphosphine Compounds

A bisphosphine compound represented by Formula (4), which is used herein as the ligand of the iron compound, can be prepared, for example, as follows:

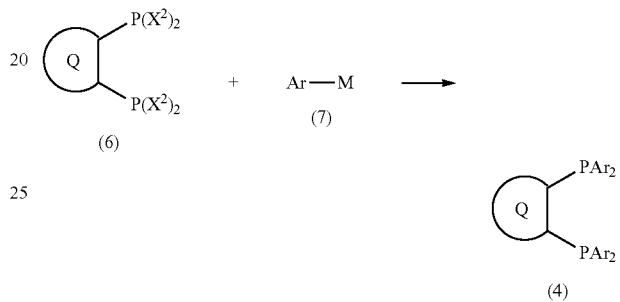

wherein each $X^2$ is a halogen atom; M is Li or a group represented by the formula: $MgY^1$, with $Y^1$ being a halogen atom, and Q and each Ar are as defined above.

Examples of Q in Formula (6) include those listed above. Preferably, Q is a group represented by the formula:

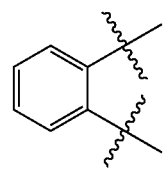 [SMILES: *c1ccccc1*]

Preferred is a compound wherein, in Formulae (4) and (7), each Ar is independently represented by the formula:

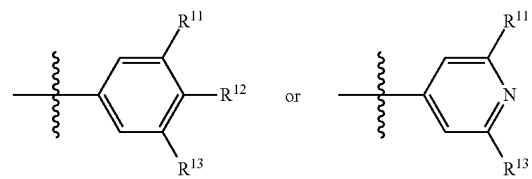

wherein $R^{11}$, $R^{12}$, and $R^{13}$ are as defined above.

Compounds wherein each Ar is substituted phenyl (the group shown above on the left), with the proviso that two of $R^{11}$, $R^{12}$, and $R^{13}$ on the phenyl are not H, and that the remaining one of them is not methyl, ethyl, or propyl, are novel.

In particular, where $R^{12}$ is H, and $R^{11}$ and $R^{13}$ are $C_1$-$C_6$ alkyl or trialkylsilyl, cross-coupling reactions using the iron compound can be significantly promoted.

Among the compounds represented by Formula (4), preferred compounds include those represented by Formula (4a), and more preferred compounds include those represented by Formula 4b).

In Formula (6), each $X^2$ is a halogen atom such as F, Cl, Br, or I, and preferably Cl. In Formula (7), where M is a group represented by the formula: $MgY^1$, $Y^1$ is a halogen atom such as Cl, Br, I, or the like, preferably Cl or Br, and more preferably Cl.

In this reaction, a compound represented by Formula (6) is reacted with a metal reagent represented by Formula (7) to thereby produce a bisphosphine compound represented by Formula (4).

Examples of reaction solvents include ether solvents such as diethylether, diisopropylether, dibutylether, tert-butyl methyl ether, cyclopentyl methyl ether, tetrahydrofuran (THF), 1,4-dioxane, and dimethoxyethane; aromatic hydrocarbon solvents such as benzene, toluene, and xylene; and mixtures thereof. Tetrahydrofuran (THF) is preferred. The concentration of a solution of the magnesium reagent may typically be about 0.5 to 1.5 mol/L.

The amount of the metal reagent represented by Formula (7) is typically 4 to 12 mol, and preferably 6 to 9 mol, per mole of the compound represented by Formula (6).

Metal reagents represented by Formula (7), wherein M is Li, can be prepared in accordance with the teachings of *The Fifth Series of Experimental Chemistry*, vol. 18, pp. 8-58; and metal reagents represented by Formula (7), wherein M is $MgY^1$ (Grignard reagents), can be prepared in accordance with the teachings of *The Fifth Series of Experimental Chemistry*, vol. 18, pp. 59-76.

Typically, the reaction is preferably conducted under anhydrous conditions in an inert gas (e.g., argon or nitrogen) atmosphere. The reaction temperature when adding the metal reagent represented by Formula (7) is typically −100 to 80° C., preferably −80 to 30° C., and more preferably −80 to 0° C. If necessary, the reaction mixture may be subsequently heated to about 0 to 100° C. for further reaction. The reaction pressure is not particularly limited; typically, atmospheric pressure is used.

After the reaction, the reaction mixture is quenched with a protonic solvent (e.g., water, ammonium chloride solution, or dilute hydrochloric acid) and extracted; if necessary, the extract is subjected to a purification procedure such as column chromatography, distillation, recrystallization, trituration, or the like, thereby giving the target bisphosphine compound represented by Formula (4).

EXAMPLES

The present invention will be described in greater detail with reference to examples; however, the invention is not limited thereto. The bisphosphine compounds are hereinafter sometimes denoted as "L" (ligand).

Production Example 1

1,2-Bis(bis(4-fluorophenyl)phosphino)benzene

A THF solution (26.6 mL, 1.03 M, 27.40 mmol) of p-fluorophenylmagnesium bromide was added to a mixture of 1,2-bis(dichlorophosphino)benzene (0.96 g, 3.43 mmol) and THF (20 mL) in an argon atmosphere at −78° C. After warming to room temperature, the mixture was allowed to react overnight at 60° C. The reaction mixture was cooled to ambient temperature, and the solvent was removed under reduced pressure; subsequently, $CH_2Cl_2$ (30 mL) was added. 1N aqueous solution of hydrochloric acid (20 mL) was added to the reaction mixture, and the aqueous layer was extracted three times with $CH_2Cl_2$. The moisture contained in the combined organic extract was removed with magnesium sulfate, and the extract was filtered. After removing the solvent under reduced pressure, the resulting yellow oily substance was triturated with methanol to give a white powder, and the white powder was washed two times with methanol, giving the title compound as a white powder (1.10 g, yield 62%).

$^1$H NMR ($CDCl_3$) δ 6.90-6.96 (m, 8H), 6.99-7.03 (m, 2H), 7.04-7.14 (m, 8H), 7.28-7.32 (m, 2H); $^{13}$C NMR ($CDCl_3$) δ 115.6 (dt, J=4.0, 20.8 Hz, 8C), 129.3 (2C), 131.9 (d, J=2.3 Hz, 4C), 133.8 (dd, J=3.1, 3.5 Hz, 2C), 135.7 (dt, J=8.0, 10.8 Hz, 8C), 143.2 (dd, J=9.7, 10.0 Hz, 2C), 163.2 (d, J=247.6 Hz, 4C); $^{31}$P NMR ($CDCl_3$) δ −17.6. Anal. calcd for $C_{30}H_{20}F_4P_2$; C, 69.50; H, 3.89. Found C, 69.77; H, 4.08.

Production Example 2

1,2-Bis(bis(4-methoxyphenyl)phosphino)benzene 1,2-Bis(dichlorophosphino)benzene (0.96 g, 3.43 mmol) and a THF solution (30.0 mL, 0.88 M, 26.40 mmol) of p-methoxyphenylmagnesium bromide were used as starting materials, and reacted as in Production Example 1. The reaction was allowed to proceed overnight at 40° C. After purification, the title compound was obtained as a white powder (1.53 g, yield 79%).

$^1$H NMR ($CDCl_3$) δ 3.77 (brs, 12H), 6.71 (brs, 4H), 6.75 (brs, 4H), 7.00-7.09 (m, 10H), 7.21-7.26 (m, 2H); $^{13}$C NMR ($CDCl_3$) δ 55.0 (4C), 113.9 (dd, J=4.0 Hz, 8C), 128.0 (4C), 128.5 (2C), 133.6 (dd, J=3.1 Hz, 2C), 135.4 (dd, J=10.8 Hz, 8C), 144.2 (dd, J=9.4 Hz, 2C), 159.7 (4C); $^{31}$P NMR ($CDCl_3$) δ −18.7. Anal. calcd for $C_{34}H_{20}O_4P_2$; C, 72.08; H, 5.67. Found C, 71.91; H, 5.75.

Production Example 3

1,2-Bis(bis(2-methylphenyl)phosphino)benzene 1,2-Bis(dichlorophosphino)benzene (0.94 g, 3.36 mmol) and a THF solution (26.6 mL, 0.80 M, 27.40 mmol) of o-methylphenylmagnesium bromide were used as starting materials, and reacted as in Production Example 1. The reaction was allowed to proceed overnight at 60° C. After purification, the title compound was obtained as a white powder (0.84 g, yield 50%).

$^1$H NMR ($CDCl_3$) δ 2.20 (brs, 12H), 6.74 (dd, J=1.5, 7.8 Hz, 4H), 6.93 (dq, J=3.6, 5.7 Hz, 2H), 7.00 (dt, J=1.2, 7.5 Hz, 4H), 7.15 (dt, J=1.2, 7.5 Hz, 4H), 7.17 (dq, J=1.5, 7.8 Hz, 4H), 7.23 (dd, J=3.6, 5.7 Hz, 2H); $^{13}$C NMR ($CDCl_3$) δ 21.1 (dd, J=10.9 Hz, 4C), 125.7 (4C), 128.3 (4C), 129.1 (2C), 129.8 (dd, J=2.3 Hz, 4C), 133.5 (4C), 133.8 (dd, J=3.2 Hz, 2C), 135.3 (dd, J=3.1 Hz, 4C), 142.6 (dd, J=13.1 Hz, 4C), 142.8 (dd, J=12.2 Hz, 2C); $^{31}$P NMR ($CDCl_3$) δ −28.5.

Production Example 4

1,2-Bis(bis(3,5-dimethylphenyl)phosphino)benzene 3,5-Dimethylbromobenzene (5.54 g, 29.93 mmol) was added dropwise to magnesium (1.07 g, 44.03 mmol) and THF (30 mL) in an argon atmosphere. The reaction mixture was cooled to ambient temperature and filtered, and the thus-obtained THF solution of 3,5-dimethylphenylmagnesium bromide, and 1,2-bis(dichlorophosphino)benzene (0.95 g, 3.39 mmol) were reacted as in Production Example 1. The reaction was allowed to proceed overnight at 60° C. After purification, the title compound was obtained as a white powder (1.45 g, yield 76%).

$^1$H NMR (CDCl$_3$) δ 2.18 (brs, 24H), 6.78 (brs, 8H), 6.86 (brs, 4H), 7.06-7.13 (m, 2H), 7.24-7.26 (m, 2H); $^{13}$C NMR (CDCl$_3$) δ 21.3 (8C), 128.7 (2C), 130.0 (4C), 131.6 (dd, J=10.0, 10.2 Hz, 8C), 134.0 (dd, 2.9, 3.2 Hz, 2C), 137.0 (dd, J=2.6 Hz, 4C), 137.4 (dd, J=3.7 Hz, 8C), 144.1 (dd, J=10.0, 10.2 Hz, 2C); $^{31}$P NMR (CDCl$_3$) δ −15.0. Anal. calcd for C$_{38}$H$_{16}$P$_2$; C, 81.69; H, 7.22. Found C, 81.40; H, 7.22.

Production Example 5

1,2-Bis(bis(3,5-diisopropylphenyl)phosphino)benzene 3,5-Diisopropylbromobenzene (3.04 g, 12.60 mmol) was added dropwise to magnesium (0.48 g, 19.75 mmol) and THF (7 mL) in an argon atmosphere. After the dropwise addition, the mixture was heated under reflux for 1 hour. The reaction mixture was cooled to ambient temperature and filtered, and the thus-obtained THF solution of 3,5-diisopropylphenylmagnesium bromide, and 1,2-bis(dichlorophosphino)benzene (0.45 g, 1.61 mmol) were reacted as in Production Example 1. The reaction was allowed to proceed overnight at 60° C. After purification, the title compound was obtained as a yellow oily substance (1.18 g, yield 74%).

$^1$H NMR (CDCl$_3$) δ 1.11 (s, 24H), 1.14 (s, 24H), 2.69-2.79 (m, 8H), 6.86-6.89 (m, 8H), 6.94 (brs, 12H), 7.01-7.09 (m, 2H), 7.22-7.26 (m, 2H); $^{13}$C NMR (CDCl$_3$) δ 23.9 (8C), 24.0 (8C), 34.0 (8C), 124.4 (4C), 128.6 (2C), 129.4 (dd, J=9.9 Hz, 8C), 133.8 (t, J=2.8, 2.9 Hz, 2C), 137.5 (dd, J=2.9 Hz, 4C), 144.6 (dd, J=10.2, 10.3 Hz, 2C), 148.2 (dd, J=3.2, 3.4 Hz, 8C); $^{31}$P NMR (CDCl$_3$) δ −12.8.

Production Example 6

1,2-Bis(bis(3,5-di-tert-butylphenyl)phosphino)benzene 3,5-Di-tert-butylbromobenzene (12.50 g, 46.43 mmol) was added dropwise to magnesium (1.70 g, 69.96 mmol) and THF (50 mL) in an argon atmosphere. After the dropwise addition, the mixture was heated under reflux for 1 hour. The reaction mixture was cooled to ambient temperature and filtered, and the thus-obtained THF solution of 3,5-di-tert-butylphenylmagnesium bromide, and 1,2-bis(dichlorophosphino)benzene (2.00 g, 7.15 mmol) were reacted as in Production Example 1. The reaction was allowed to proceed overnight at 60° C. After purification, the title compound was obtained as a white powder (4.66 g, yield 73%).

$^1$H NMR (CDCl$_3$) δ 1.18 (brs, 72H), 7.00-7.07 (m, 10H), 7.21-7.24 (m, 2H), 7.27-7.30 (m, 4H); $^{13}$C NMR (CDCl$_3$) δ 31.4 (24C), 34.8 (8C), 121.9 (4C), 128.0 (dd, J=10.0 Hz, 8C), 128.5 (2C), 133.8 (2C), 137.0 (dd, J=2.6 Hz, 4C), 144.8 (dd, J=10.0, 10.2 Hz, 2C), 150.0 (dd, J=3.2, 3.5 Hz, 8C); $^{31}$P NMR (CDCl$_3$) δ −11.4. Anal. calcd for C$_{62}$H$_{88}$P$_2$; C, 83.17; H, 9.91. Found C, 83.17; H, 9.92.

Production Example 7

1,2-Bis(bis(3,5-bis(2,6-dimethylphenyl)phenyl)phosphino)benzene

1-Bromo-3,5-bis(2,6-dimethylphenyl)benzene (2.74 g, 7.50 mmol) was added dropwise to magnesium (0.28 g, 11.52 mmol) and THF (10 mL) in an argon atmosphere. After the dropwise addition, the mixture was heated under reflux for 1 hour. The reaction mixture was cooled to ambient temperature and filtered, and the thus-obtained THF solution of 1-(3,5-bis(2,6-dimethylphenyl))magnesium bromide, and 1,2-bis (dichlorophosphino)benzene (0.28 g, 1.00 mmol) were reacted as in Production Example 1. The reaction was allowed to proceed overnight at 60° C. After purification, the title compound was obtained as a yellow powder (0.70 g, yield 62%).

$^1$H NMR (CDCl$_3$) δ 1.90 (brs, 48H), 6.66-7.51 (m, 40H); $^{31}$P NMR (CDCl$_3$) δ −11.8.

Production Example 8

1,2-Bis(bis(3,5-ditrimethylsilylphenyl)phosphino)benzene 3,5-Ditrimethylsilylbromobenzene (2.51 g, 8.33 mmol) was added dropwise to magnesium (0.31 g, 12.76 mmol) and THF (7 mL) in an argon atmosphere. After the dropwise addition, the mixture was heated at 40° C. for 1.5 hours. The reaction mixture was cooled to ambient temperature and filtered, and the thus-obtained THF solution of 3,5-ditrimethylsilylphenylmagnesium bromide and 1,2-bis(dichlorophosphino)benzene (0.37 g, 1.32 mmol) were reacted as in Production Example 1. The reaction was allowed to proceed overnight at 60° C. After purification, the title compound was obtained as a white powder (0.84 g, yield 62%).

$^1$H NMR (CDCl$_3$) δ 0.13 (brs, 72H), 7.03-7.09 (m, 2H), 7.25-7.29 (m, 10H), 7.54 (brs, 4H); $^{13}$C NMR (CDCl$_3$) δ −1.1 (24C), 128.8 (2C), 133.9 (2C), 136.0 (dd, J=4.0 Hz, 4C), 137.8 (4C), 138.9 (dd, J=2.3 Hz, 8C), 139.1 (dd, J=9.4, 9.7 Hz, 8C), 144.0 (dd, J=10.0, 10.1 Hz, 2C); $^{31}$P NMR (CDCl$_3$) δ −13.7; Anal. calcd for C$_{54}$H$_{88}$P$_2$Si$_8$; C, 63.34; H, 8.66. Found C, 63.50; H, 8.71.

Production Example 9

1,2-Bis(diphenylphosphino)benzene

A product of Aldrich was used as this compound: CAS No: 13991-08-7.

Production Example 10

2,3-Bis(diphenylphosphino)quinoxaline (DPP-Quinox)

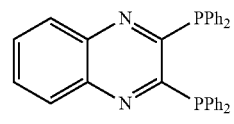

A hexane solution (7.5 mL, 1.6 M, 12.00 mmol) of n-butyllithium was added to a hexane solution (22.3 g, 10 wt %, 16.06 mmol) of diphenylphosphine in an argon atmosphere at −78° C. over 10 minutes. The mixture was warmed to room temperature and stirred for 1 hour; 2,3-dichloroquinoxaline (0.79 g, 3.97 mmol) was subsequently dissolved in THF (24 mL) and added to the stirred mixture at −78° C. over 30 minutes. The mixture was warmed to room temperature and allowed to react for 3 hours.

1N aqueous solution of hydrochloric acid (30 mL) was added to the reaction mixture, the aqueous layer was extracted three times with EtOAc, and the combined organic layer was washed with saturated brine. The moisture contained in the combined organic extract was removed with magnesium sulfate, and the extract was filtered. After removing the solvent under reduced pressure, the resulting red-orange solid was recrystallized from toluene, giving the title compound as an orange powder (0.89 g, yield 45%).

$^1$H NMR (CDCl$_3$) δ 7.24-7.34 (m, 20H), 7.63-7.66 (m, 2H), 7.89-7.93 (m, 2H); $^{13}$C NMR (CDCl$_3$) δ 128.1 (dd, J=3.7, 3.8 Hz, 8C), 128.7 (4C), 129.7 (2C), 129.9 (2C), 134.6 (dd, J=10.2, 10.3 Hz, 8C), 135.6 (4C), 142.2 (2C), 163.8 (dd, J=9.2, 10.2 Hz, 2C); $^{31}$P NMR (CDCl$_3$) δ −10.7. Anal. calcd for C$_{32}$H$_{24}$N$_2$P$_2$; C, 77.10; H, 4.85; N, 5.62. Found C, 77.32; H, 4.94; N, 5.57.

The compounds produced in Production Examples 1 to 8 are shown in Table 1.

TABLE 1

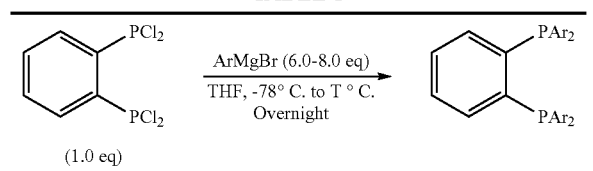

(1.0 eq)

| Production Example | ArMgBr | Yield (%) (T °C.) | Abbreviated Formula of Product |
|---|---|---|---|
| 1 | 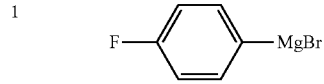 | 62 (60° C.) | [4-F]-DPPBz |
| 2 | 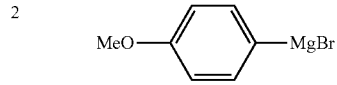 | 79 (40° C.) | [4-MeO]-DPPBz |
| 3 | 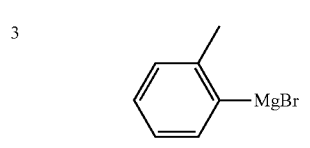 | 50 (60° C.) | [2-Me]-DPPBz |
| 4 | 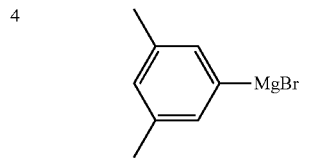 | 76 (60° C.) | [3,5-Me$_2$]-DPPBz |
| 5 | 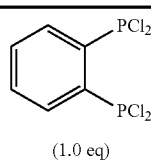 | 74 (60° C.) | [3,5-(i-Pr)$_2$]-DPPBz |

TABLE 1-continued

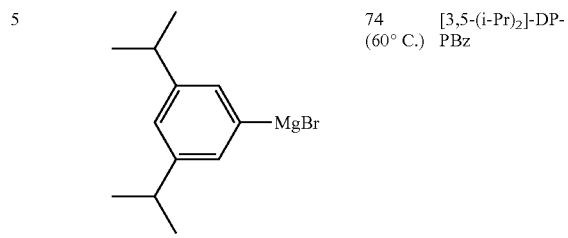

(1.0 eq)

| Production Example | ArMgBr | Yield (%) (T °C.) | Abbreviated Formula of Product |
|---|---|---|---|
| 6 | 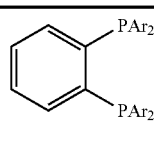 | 73 (60° C.) | [3,5-(t-Bu)$_2$]-DPPBz |
| 7 | 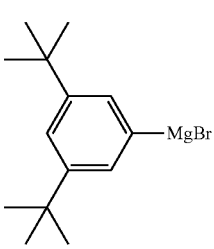 | 54 (60° C.) | [3,5-Ar$_2$]-DPPBz |
| 8 | 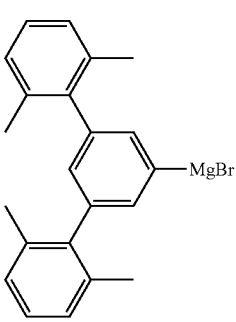 | 62 (60° C.) | [3,5-(Me$_3$Si)$_2$]-DPPBz |

Example 1

(1) Iron chloride.1,2-Bis(bis(3,5-di-tert-butylphenyl)phosphino)benzene Complex (FeCl$_2$.L)

1,2-Bis(bis(3,5-di-tert-butylphenyl)phosphino)benzene (1.00 g, 1.12 mmol) was added to FeCl$_2$.4H$_2$O (0.22 g, 1.11 mmol) and ethanol (25 mL) in an argon atmosphere. The following procedure was also performed in the argon atmosphere. The reaction was performed at 90° C. for 6 hours. The reaction mixture was cooled to ambient temperature, and the solvent was removed under reduced pressure. The resulting white powder was washed three times with ethanol, filtered, and dried under reduced pressure. The title compound was obtained as a white powder (0.70 g, yield 61%). FIG. 1 shows the structure (ORTEP) of the title compound as determined by X-ray analysis.

$^1$H NMR(C$_4$D$_8$O) δ −5.83 (brs, 6H), −1.19-2.56 (brs, 74H), 4.54 (brs, 4H), 7.08-7.76 (m, 2H), 15.34 (brs, 2H); Anal. calcd for C$_{62}$H$_{88}$Cl$_2$FeP$_2$; C, 72.86; H, 8.68. Found C, 72.60; H, 8.75.

(2) Iron chloride.1,2-Bis(bis(3,5-dimethylphenyl)phosphino)benzene Complex (FeCl$_2$.L)

Figure 3:
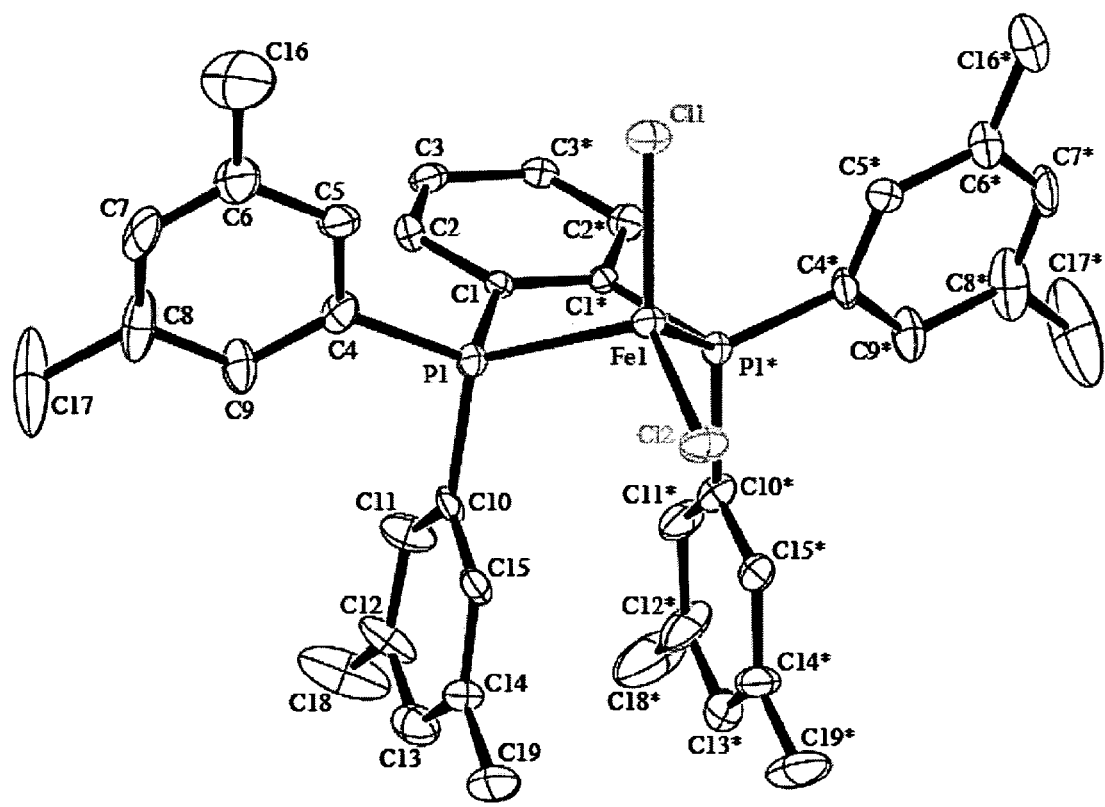
FIG. 3 shows the structure (ORTEP) of iron chloride.1,2-bis(bis(3,5-dimethylphenyl)phosphino)benzene complex ($FeCl_2$.L) produced in Example 1 (2), as determined by X-ray analysis.

1,2-Bis(bis(3,5-dimethylphenyl)phosphino)benzene (586 mg, 1.05 mmol) was added to FeCl$_2$ (127 mg, 1.00 mmol) and THF (10 mL) in an argon atmosphere. The following procedure was also performed in the argon atmosphere. The reaction was performed at 80° C. for 6 hours. The reaction mixture was cooled to ambient temperature, and the solvent was removed under reduced pressure. The crude product was dissolved in dichloromethane and filtered, and the solvent was removed under reduced pressure. The resulting brown-white powder was washed three times with diethylether, and dried under reduced pressure. The title compound was obtained as a pale brown-white powder (365 mg, yield 53%). FIG. 3 shows the structure (ORTEP) of the title compound as determined by X-ray analysis.

$^1$H NMR (CDCl$_2$) δ –5.62 (brs, 6H), –1.66 (brs, 26H), 3.22 (brs, 2H), 7.00 (m, 2H), 14.92 (brs, 2H); Anal. calcd for C$_{38}$H$_{40}$Cl$_2$FeP$_2$; C, 66.59; H, 5.88. Found C, 66.17; H, 5.87.

Example 2

Cross-Coupling Reaction

Using the reagent(s) selected from the iron chloride.1,2-bis(bis(3,5-di-tert-butylphenyl)phosphino)benzene complex (FeCl$_2$.L) obtained in Example 1 (1), iron chloride (FeCl$_3$), and a ligand (L) 1,2-bis(bis(3,5-di-tert-butylphenyl)phosphino)benzene complex; bromocycloheptane and phenylmagnesium bromide were reacted under the conditions shown in Table 2. The products and yields thereof are shown in Table 2. The yields were determined by GC using undecane as an internal standard.

Specifically, bromocycloheptane was added at 0° C. to a THF solution containing FeCl$_2$.L or FeCl$_3$, and, optionally containing L, in an argon atmosphere. THF was further added to rinse the inside wall of the reactor. A THF solution of phenylmagnesium bromide was added dropwise to the mixture at 25° C. via a syringe pump over 20 minutes, and the mixture was stirred at 25° C. for 10 minutes and allowed to react.

TABLE 2

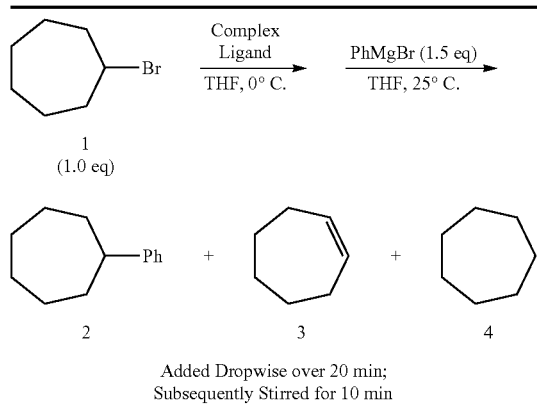

Added Dropwise over 20 min;
Subsequently Stirred for 10 min

| Entry | Complex (mol %) | Additional Complex (mol %) | GC Yield (%) 2 | 3 | 4 | 1 |
| --- | --- | --- | --- | --- | --- | --- |
| 1 | FeCl$_2$•L (0.5) | None | 85 | 13 | 0 | 2 |
| 2 | FeCl$_2$•L (0.5) | L (0.5) | 92 | 8 | 0 | 0 |
| 3 | FeCl$_3$ (0.5) | L (1) | 92 | 7 | 0 | 0 |

Example 3

Cross-Coupling Reaction (Influence of the Ligand)

Using each of the ligands obtained in Production Examples 1 to 9 and iron chloride (FeCl$_3$), bromocycloheptane and a THF solution of phenylmagnesium bromide were reacted under the conditions shown in Table 3. The products and yields thereof are shown in Table 3. The yields were determined by GC using undecane as an internal standard.

Specifically, bromocycloheptane was added at 0° C. to a THF solution containing FeCl$_3$ and optionally each of the various ligands in an argon atmosphere. THF was further added to rinse the inside wall of the reactor. A THF solution of phenylmagnesium bromide was added dropwise to the mixture at 25° C. via a syringe pump over 20 minutes, and the mixture was stirred at 25° C. for 10 minutes and allowed to react.

TABLE 3

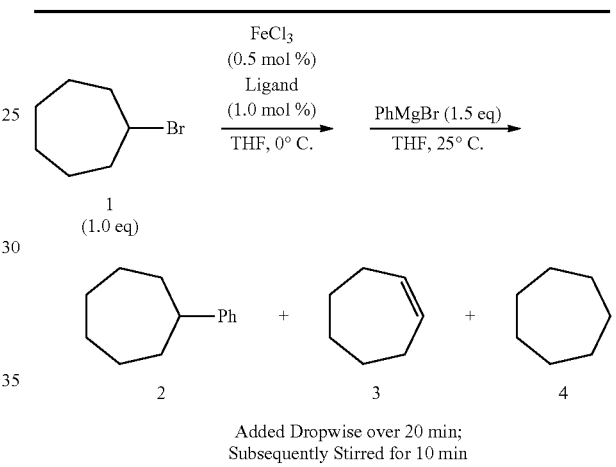

Added Dropwise over 20 min;
Subsequently Stirred for 10 min

| Entry | Ligand | Yield (%) 2 | 3 | 4 | 1 |
| --- | --- | --- | --- | --- | --- |
| 1 | None | 21 | 69 | 6 | 0 |
| 2 | DPPBz | 55 | 15 | 1 | 23 |
| 3 | [4-F]-DPPBz | 38 | 16 | 2 | 34 |
| 4 | [4-MeO]-DPPBz | 29 | 9 | 1 | 56 |
| 5* | DPP-Quinox | 24 | 31 | 15 | 0 |
| 6 | [2-Me]-DPPBz | 19 | 66 | 5 | 0 |
| 7 | [3,5-Me$_2$]-DPPBz | 83 | 17 | 0 | 0 |
| 8 | [3,5-(i-Pr)$_2$]-DPPBz | 84 | 16 | 0 | 0 |
| 9 | [3,5-(t-Bu)$_2$]-DPPBz | 92 | 7 | 0 | 0 |
| 10 | [3,5-Ar$_2$]-DPPBz** | 14 | 44 | 8 | 16 |
| 11 | [3,5-(Me$_3$Si)$_2$]-DPPBz | 83 | 13 | 0 | 4 |

*The reaction was performed using FeCl$_3$ (3 mol %), the ligand (6 mol %), and PhMgBr (2.4 eq) by adding the PhMgBr dropwise at 60° C. over 30 min.
**Ar represents 2,6-dimethylphenyl.

The results revealed that Cross-Coupling Compound (2) was produced with high yield and high selectivity in Entries 7, 8, 9, and 11.

Example 4

Cross-Coupling Reaction

[Entry 1] Preparation of Cyclohexylbenzene

Iron chloride.1,2-bis(bis(3,5-di-tert-butylphenyl)phosphino)benzene complex (FeCl$_2$.L) (2.5 mg, 2.5 μmol), 1,2-bis(bis(3,5-di-tert-butylphenyl)phosphino)benzene (L) (2.2 mg, 2.5 µmol), and bromocyclohexane (81.5 mg, 0.5 mmol) were mixed at 0° C. in an argon atmosphere. The following procedure was also performed in the argon atmosphere. THF (0.80 mL) was added to rinse the inside wall of the reactor. A THF solution of phenylmagnesium bromide (0.77 mL, 0.97 M, 0.75 mmol) was added dropwise to the mixture at 25° C. via a syringe pump over 20 minutes and reacted. The reaction mixture was further stirred at 25° C. for 10 minutes, and cooled to 0° C.; 2.0 mL of a saturated aqueous solution of ammonium chloride was subsequently added. The aqueous layer was extracted four times with hexane. The combined organic extract was filtered using a Florisil pad (100-200 mesh, Nacalai Tesque, Inc.). The solvent was removed under reduced pressure, and $^1$H-NMR analysis was conducted using pyrazine (15.3 mg, 0.19 mmol) as an internal standard (yield 97%).

[Entry 2] Preparation of Cyclohexylbenzene

Chlorocyclohexane (59.5 mg, 0.5 mmol) and a THF solution (0.77 mL, 0.97 M, 0.75 mmol) of phenylmagnesium bromide were used as starting materials, and reacted as in Entry 1. Conditions: The THF solution of phenylmagnesium bromide was added dropwise at 40° C. over 2 hours. $^1$H-NMR analysis was conducted using pyrazine (19.4 mg, 0.24 mmol) as an internal standard (yield 85%).

[Entry 3] Preparation of (2-Methylphenyl)cyclohexane

Bromocyclohexane (81.7 mg, 0.5 mmol) and a THF solution (0.94 mL, 0.80 M, 0.75 mmol) of 2-methylphenylmagnesium bromide were used as starting materials, and reacted as in Entry 1. Conditions: The THF solution of 2-methylphenylmagnesium bromide was added dropwise at 40° C. over 20 minutes. $^1$H-NMR analysis was conducted using pyrazine (13.2 mg, 0.16 mmol) as an internal standard (yield 99%).

[Entry 4] Preparation of (3,4,5-Trifluorophenyl)cyclohexane

Bromocyclohexane (81.5 mg, 0.5 mmol) and a THF solution (0.84 mL, 0.89 M, 0.75 mmol) of 3,4,5-phenylmagnesium bromide were used as starting materials, and reacted as in Entry 1. Conditions: The THF solution of 3,4,5-phenylmagnesium bromide was added dropwise at 40° C. over 20 minutes. After silica gel column chromatography (pentane), the title compound was obtained as a colorless liquid (0.207 g, yield 98%).
$^1$H NMR (CDCl$_3$) δ 1.15-1.45 (m, 5H), 1.72-1.86 (m, 5H), 2.40-2.48 (m, 1H), 6.74-6.85 (m, 2H); $^{13}$C NMR (CDCl$_3$) δ 25.9, 26.5 (2C), 34.2 (2C), 43.9, 110.5 (dt, J=5.5, 15.0 Hz, 2C), 137.8 (dt, J=15.5, 246.4 Hz), 144.2 (dt, J=4.9, 6.7 Hz), 151.0 (ddd, J=4.5, 9.4, 247.1 Hz, 2C). Anal. calcd for C$_{12}$H$_{13}$F$_3$C, 67.28; H, 6.12. Found C, 67.29; H, 6.10.

[Entry 5] Preparation of (4-Methoxyphenyl)cyclohexane

Bromocyclohexane (81.8 mg, 0.5 mmol) and a THF solution (0.85 mL, 0.88 M, 0.75 mmol) of 4-methoxyphenylmagnesium bromide were used as starting materials, and reacted as in Entry 1. Conditions: The THF solution of 4-methoxyphenylmagnesium bromide was added dropwise at 25° C. over 20 minutes. $^1$H-NMR analysis was conducted using pyrazine (19.0 mg, 0.24 mmol) as an internal standard (yield 96%).

[Entry 6] Preparation of Decylbenzene

1-Iododecane (134.1 mg, 0.5 mmol) and a THF solution (0.77 mL, 0.97 M, 0.75 mmol) of phenylmagnesium bromide were used as starting materials, and reacted as in Entry 1. Conditions: The THF solution of phenylmagnesium bromide was added dropwise at 40° C. over 2 hours. $^1$H-NMR analysis was conducted using pyrazine (29.0 mg, 0.36 mmol) as an internal standard (yield 71%).

[Entry 7] Preparation of 1-Decyl-2,4,6-trimethylbenzene

1-Iododecane (133.9 mg, 0.5 mmol) and a THF solution (0.66 mL, 1.14 M, 0.75 mmol) of 2,4,6-trimethylphenylmagnesium bromide were used as starting materials, and reacted as in Entry 1. Conditions: The THF solution of 2,4,6-trimethylphenylmagnesium bromide was added dropwise at 40° C. over 3 hours. After thin-layer chromatography (hexane), the title compound was obtained as a colorless liquid (0.121 g, yield 93%).
$^1$H NMR δ 0.88 (t, J=6.5 Hz, 3H), 1.27-1.40 (m, 16H), 2.24 (s, 3H), 2.28 (s, 6H), 2.55 (t, J=7.8 Hz, 3H), 6.82 (s, 2H); $^{13}$C NMR δ 14.1, 19.7 (2C), 20.8, 22.7, 29.3 (2C), 29.4, 29.5, 29.6 (2C), 30.3, 31.9, 128.8 (2C), 134.7, 135.8 (2C), 136.7; Anal. calcd for C$_{19}$H$_{32}$C, 87.62; H, 12.38. Found C, 87.39; H, 12.47.

[Entry 8] Preparation of 1-Decyl-2,4,6-trimethylbenzene

1-Bromodecane (110.8 mg, 0.5 mmol) and a THF solution (0.66 mL, 1.14 M, 0.75 mmol) of 2,4,6-trimethylphenylmagnesium bromide were used as starting materials, and reacted as in Entry 1. Conditions: The THF solution of 2,4,6-trimethylphenylmagnesium bromide was added dropwise at 40° C. over 3 hours. After thin-layer chromatography (hexane), the title compound was obtained as a colorless liquid (0.099 g, yield 76%).

[Entry 9] Preparation of 1-Phenyladamantane

1-Bromoadamantane (215.4 mg, 1.0 mmol) and a THF solution (1.55 mL, 0.97 M, 1.50 mmol) of phenylmagnesium bromide were used as starting materials, and reacted as in Entry 1. Conditions: The THF solution of phenylmagnesium bromide was added dropwise at 40° C. over 3 hours. After silica gel column chromatography (pentane), the title compound was obtained as a white solid (0.173 g, yield 81%).

[Entry 10] Preparation of 4-(4-Bromophenethyl)-1-methoxybenzene

4-Bromophenethyl bromide (261.4 mg, 1.0 mmol) and a THF solution (1.42 mL, 1.06 M, 1.5 mmol) of 4-methoxyphenylmagnesium bromide were used as starting materials, and reacted as in Entry 1. Conditions: The THF solution of 4-methoxyphenylmagnesium bromide was added dropwise at 40° C. over 3 hours. After thin-layer chromatography (hexane/ethyl acetate=92/8), the title compound was obtained as a colorless liquid (0.226 g, yield 78%).
$^1$H NMR δ 2.84 (brs, 4H), 3.79 (s, 3H), 6.79-6.84 (m, 2H), 6.99-7.08 (m, 4H), 7.36-7.40 (m, 2H); $^{13}$C NMR δ 36.7, 37.5, 55.2, 113.7 (2C), 129.3 (2C), 130.3 (2C), 131.3 (2C), 133.3, 140.7, 157.9. Anal. calcd for C$_{15}$H$_{15}$BrO C, 61.87; H, 5.19. Found C, 62.13; H, 5.27.

TABLE 4

$$R-X \xrightarrow[\text{THF, 0°C.}]{\text{FeCl}_2\cdot L \text{ (Y mol \%)} \atop \text{And L (Y mol \%)}} \xrightarrow[\text{THF}]{\text{Ar'MgBr (1.5 eq)}} R-Ar'$$

(1.0 eq)

Added Slowly;
Subsequently Stirred for 10 min

| Entry | R—X | Ar'MgBr | Y mol % | Yield of R—Ar' (%) (Temperature, Dropwise Addition Time) |
|---|---|---|---|---|
| 1 | cyclohexyl-Br | Ph-MgBr | 0.5 mol % | 97 (25° C., 20 min) |
| 2 | cyclohexyl-Cl | Ph-MgBr | 3.0 mol % | 85 (40° C., 2 h) |
| 3 | cyclohexyl-Br | o-tolyl-MgBr | 3.0 mol % | 99 (40° C., 20 min) |
| 4 | cyclohexyl-Br | 3,4,5-trifluorophenyl-MgBr | 3.0 mol % | 98 (40° C., 20 min) |
| 5 | cyclohexyl-Br | 4-MeO-C₆H₄-MgBr | 3.0 mol % | 96 3.0 mol % (25° C., 20 min) |
| 6 | CH₃(CH₂)₈CH₂-I | Ph-MgBr | 3.0 mol % | 71 (40° C., 2 h) |
| 7 | CH₃(CH₂)₈CH₂-I | 2,4,6-trimethylphenyl-MgBr | 3.0 mol % | 93 (40° C., 3 h) |
| 8 | CH₃(CH₂)₈CH₂-Br | 2,4,6-trimethylphenyl-MgBr | 3.0 mol % | 76 (40° C., 3 h) |
| 9 | 1-adamantyl-Br | Ph-MgBr | 3.0 mol % | 81 (40° C., 3 h) |

TABLE 4-continued $$R-X \xrightarrow[\text{THF, 0° C.}]{\text{FeCl}_2 \cdot L \text{ (Y mol \%)} \atop \text{And L (Y mol \%)}} \xrightarrow{\text{Ar'MgBr (1.5 eq)} \atop \text{THF}} R-Ar'$$

(1.0 eq)

Added Slowly;
Subsequently Stirred for 10 min

| Entry | R—X | Ar'MgBr | Y mol % | Yield of R—Ar' (%) (Temperature, Dropwise Addition Time) |
|---|---|---|---|---|
| 10 | 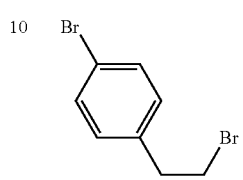 | MeO—⟨benzene⟩—MgBr | 3.0 mol % | 78 (40° C., 3 h) | a: Isolated yield
b: The yield was determined by ¹H NMR using pyrazine as an internal standard.
L = [3,5-(t-Bu)₂]-DPPBz Table 4 shows that, in Entries 1 to 10, the cross-coupling compounds were produced with high yields. Furthermore, it should be particularly noted that the reaction proceeded with an extremely high yield even in the case of a compound prepared using an aromatic magnesium reagent having fluorine atoms on its aromatic ring, as in Entry 4.

Example 5

Cross-Coupling Reaction (Organozinc Reagent)

A 1.14 M THF solution of phenylmagnesium bromide (1.05 mL, 1.2 mmol), 1,2-bis(bis(3,5-ditrimethylsilylphenyl)phosphino)benzene[3,5-(TMS)₂]-DPPBz (4.5 mg, 50 μmol), bromocycloheptane (88.7 mg, 0.50 mmol), and undecane (46.9 mg, 0.30 mmol) were added at 0° C. to 0.6 mL of a THF solution of zinc chloride ZnCl₂ (81.8 mg, 0.60 mmol). After 10 minutes, a 0.10 M THF solution of FeCl₃ (50.0 μL, 50 μmol) was added at 0° C. The coupling reaction was performed at 50° C. for 5 hours. After cooling to room temperature, a portion of the reaction mixture was taken out, and the yield of the product was measured by gas chromatography (GC), using undecane as an internal standard. The results are shown in the Entry 4 column of Table 5.

The reaction of Entry 1 was performed according to the same procedure as above, except that a ligand was not used.

The reactions of Entries 2 and 3 were performed according to the same procedure as above, except that 1,2-bis(diphenylphosphino)benzene (DPPBz) and 1,2-bis(bis(3,5-di-tert-butylphenyl)phosphino)benzene ([3,5-(t-Bu)₂]-DPPBz), respectively, were used as ligands.

TABLE 5

$$\text{cycloheptyl-Br} \xrightarrow[\text{(1.2 equiv)}]{\text{Ph}_2\text{Zn} \cdot 2\text{MgBrCl}} \xrightarrow[\text{THF, 50° C., 5 h}]{\text{FeCl}_3 \text{ (1 mol \%)} \atop \text{Ligand (1 mol \%)}}$$

1
(0.5 mmol)

cycloheptyl-Ph + cycloheptene + cycloheptane 2      3      4

| Entry | Ligand | GC Yield (%) | | | Collected Starting |
|---|---|---|---|---|---|
| | | 2 | 3 | 4 | Materials |
| 1 | None | 67 | 11 | 3 | 15 |
| 2 | DPPBz | 82 | 9 | 5 | 4 |
| 3 | [3,5-(t-Bu)₂]-DPPBz | 96 | 3 | 2 | 0 |
| 4 | [3,5-(TMS)₂]-DPPBz | 96 | 3 | 2 | 0 |

Example 6

Cross-Coupling Reaction (Organoboron Reagent)

A 1.62 M THF solution of t-BuLi in pentane (0.58 mL, 0.95 mmol) was added at −40° C. to 2.5 mL of a THF solution of phenylboronic acid pinacol ester (204.1 mg, 1.0 mmol). The reaction mixture was stirred at −40° C. for 30 minutes, and then stirred at 0° C. for 30 minutes. The solvent was removed at 0° C. under reduced pressure. White crystals of the residual lithium t-butyl borate were dissolved in 1.5 mL THF at 0° C. To the resulting solution of lithium t-butyl borate were added undecane (51.1 mg, 0.33 mmol), bromocycloheptane (66.9 mg, 0.50 mmol), a 0.10 M THF solution of magnesium bromide MgBr₂ (1.00 mL, 0.10 mmol), 1,2-bis(bis(3,5-di-tert-butylphenyl)phosphino)benzene ([3,5-(t-Bu)₂]DPPBz) (22.4 mg, 0.025 mmol, 5.00 mol %), and a 0.10 M THF solution of iron chloride $FeCl_3$ (250 µL, 0.025 mmol, 5.00 mol %). The coupling reaction was performed at 60° C. for 3 hours. After cooling to room temperature, a portion of the reaction mixture was taken out, and the yield of the product was measured by gas chromatography (GC), using undecane as an internal standard. The yield was 95%. The results are shown in the Entry 7 column of Table 6.

The reaction of Entry 1 was performed according to the same procedure as above, except that a ligand was not used.

The reactions of Entries 2 and 3 were performed according to the same procedure as above, except that the ligand [3,5-(t-Bu)$_2$]DPPBz was replaced with 1,2-bis(diphenylphosphino)benzene (DPPBz), and that 1,2-bis(diphenylphosphino)benzene (DPPBz) was used in amounts of 5 mol % and 10 mol % in Entries 2 and 3, respectively, based on bromocycloheptane.

The reaction of Entry 4 was performed according to the same procedure as above, except that the ligand [3,5-(t-Bu)$_2$]-DPPBz was replaced with 1,2-bis(bis(4-methoxyphenyl)phosphino)benzene ([4-MeO]-DPPBz).

The reactions of Entries 5 and 6 were performed according to the same procedure as above, except that the ligand [3,5-(t-Bu)$_2$]-DPPBz was replaced with 1,2-bis(bis(3,5-ditrimethylsilylphenyl)phosphino)benzene ([3,5-(TMS)$_2$]-DPPBz), and 1,2-bis(bis(3,5-ditrimethylsilylphenyl)phosphino)benzene ([3,5-(TMS)$_2$]-DPPBz) was used in amounts of 5 mol % and 10 mol % in Entries 5 and 6, respectively, based on bromocycloheptane.

The reaction of Entry 8 was performed according to the same procedure as above, except that the ligand [3,5-(t-Bu)$_2$]-DPPBz was used in an amount of 10 mol % based on bromocycloheptane.

TABLE 6

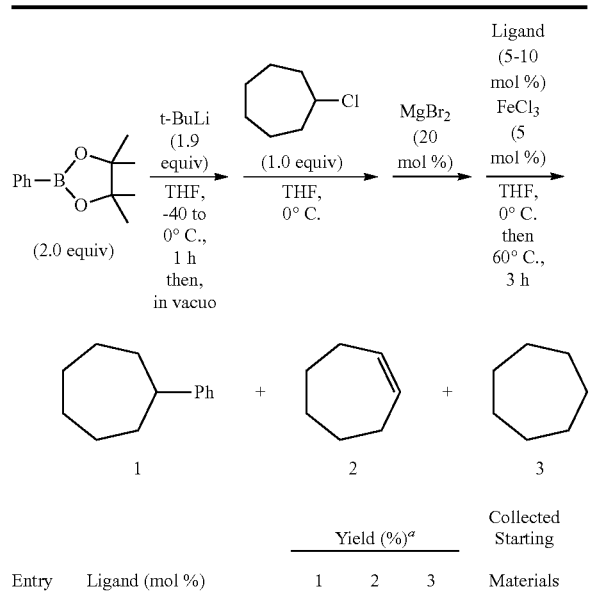

| Entry | Ligand (mol %) | Yield (%)[a] 1 | 2 | 3 | Collected Starting Materials |
|---|---|---|---|---|---|
| 1 | None | 10 | 44 | 7 | 34 |
| 2 | DPPBz (5) | 17 | 20 | 16 | 33 |
| 3 | DPPBz (10) | 4 | 3 | 8 | 85 |
| 4 | [4-MeO-DPPBz (5) | 58 | 15 | 10 | 4 |
| 5 | [3,5-(TMS)$_2$]-DPPBz (5) | 50 | 15 | 6 | 19 |
| 6 | [3,5-(TMS)$_2$]-DPPBz (10) | 96 | 0 | 0 | 0 |

TABLE 6-continued

| 7 | [3,5-(t-Bu)$_2$]-DPPBz (5) | 72 | 14 | 3 | 0 |
| 8 | [3,5-(t-Bu)$_2$]-DPPBz (10) | 95 | <2 | 0 | 0 |

[a]The yield was measured by calibrated GC analysis using undecane as an internal standard.

Example 7

Cross-Coupling Reaction (Organoboron Reagent)

One equivalent of t-BuLi (1.62 M in pentane) was added at 0° C. to a THF solution of phenylboronic acid pinacol ester. The reaction mixture was stirred at 0° C. for 30 minutes, and the solvent was subsequently removed under reduced pressure. White crystals of the residual lithium t-butyl borate were dissolved in THF, and recrystallized from THF/hexane. The resulting white crystals were collected and dissolved in THF in an argon atmosphere. This solution can be preserved at 0° C. for several weeks without decomposition. The concentration of the solution was determined by NMR using mesitylene as an internal standard.

Undecane (30.3 mg, 0.19 mmol), bromocycloheptane (67.6 mg, 0.51 mmol), a 0.100 M THF solution of anhydrous magnesium bromide $MgBr_2$ (1.00 mL, 0.10 mmol), and iron chloride.1,2-bis(bis(3,5-di-tert-butylphenyl)phosphino)benzene complex ($FeCl_2$.[3,5-(t-Bu)$_2$]-DPPBz complex) (250 µL, 0.025 mmol, 5.00 mol %) were added at 0° C. to a 0.73 M THF solution of lithium t-butyl borate (1.40 mL, 1.0 mmol). The coupling reaction was performed at 60° C. for 3 hours. After cooling to room temperature, a portion of the reaction mixture was taken out, and the yield of the product was measured by gas chromatography (GC), using undecane as an internal standard. The results are shown in the Entry 2 column of Table 7.

The reaction of Entry 1 was performed according to the same procedure as above, except that the iron chloride.1,2-bis(bis(3,5-di-tert-butylphenyl)phosphino)benzene complex ($FeCl_2$.[3,5-(t-Bu)$_2$]-DPPBz complex) was replaced with an iron chloride.[1,2-bis(diphenylphosphino)benzene]$_2$ complex ($FeCl_2$.L$_2$).

TABLE 7

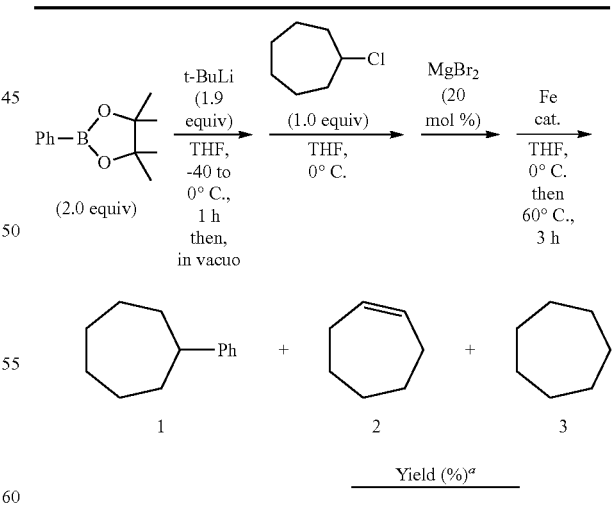

| Entry | Fe cat. (mol %) | Yield (%)[a] 1 | 2 | 3 | RSM |
|---|---|---|---|---|---|
| 1 | $FeCl_2$(dppbz)$_2$ (5) | 0 | 0 | 43 | 56[b] |
| 2 | $FeCl_2$[3,5-(t-Bu)$_2$]DPPBz (5) | 81 | 14 | 5 | 0 |

[a]The yield was measured by calibrated GC analysis using undecane as an internal standard.
[b]The yield was measured by non-calibrated GC analysis using undecane as an internal standard.

Example 8

Cross-Coupling Reaction (Organoboron Reagent)

1.80 M t-BuLi in pentane (0.78 mL, 1.40 mmol) was added at −40° C. to 5.0 mL of a THF solution of 4-methoxyphenylboronic acid pinacol ester (351.2 mg, 1.5 mmol). The reaction mixture was stirred at −40° C. for 30 minutes, and then stirred at 0° C. for 30 minutes. The solvent was removed at 0° C. under reduced pressure. White crystals of the residual lithium t-butyl borate were dissolved in 2.4 mL THF at 0° C. To the resulting solution of lithium t-butyl borate were added undecane (66.2 mg, 0.42 mmol), bromocycloheptane (178.2 mg, 1.01 mmol), a 0.10 M THF solution of magnesium bromide MgBr$_2$ (2.00 mL, 0.20 mmol), and a THF solution (0.60 ml, 0.030 mmol, 3.00 mol %) of an iron chloride.1,2-bis(bis(3,5-trimethylsilylphenyl)phosphino)benzene complex (FeCl$_2$.[3,5-(t-Bu)$_2$]-DPPBz complex). The coupling reaction was performed at 40° C. for 3 hours. The resulting reaction mixture was cooled to 0° C., and 2.0 mL of a saturated aqueous solution of ammonium chloride was subsequently added thereto. The aqueous layer was extracted five times with diethylether. The combined organic extract was filtered using a Florisil pad (100-200 mesh, Nacalai Tesque, Inc.). After thin-layer chromatography (hexane), (4-methoxyphenyl)cycloheptane was obtained as a colorless liquid (0.199 g, yield 97%).

Example 9

Cross-Coupling Reaction (Organoboron Reagent)

The reaction was performed as in Example 8, except that bromocycloheptane (89.2 mg, 0.50 mmol) and 3,4,5-trifluorophenylboronic acid pinacol ester (193.5 mg, 0.75 mmol) were used as starting materials, and that 1.80 M t-BuLi in pentane (0.39 ml, 0.70 mmol) was added at −78° C. $^1$H-NMR analysis was conducted using pyrazine (11.7 mg, 0.15 mmol) as an internal standard (yield 94%).

Example 10

Cross-Coupling Reaction (Organoaluminum Reagent)

A 1.64 M THF solution of phenylmagnesium chloride (1.10 mL, 2.40 mmol) was added at 0° C. to 0.6 mL of a THF solution of aluminum chloride $AlCl_3$ (80.0 mg, 0.60 mmol). The reaction mixture was stirred at room temperature for 1 hour. To the resulting solution was added 1,2-bis(bis(3,5-di-tert-butylphenyl)phosphino)benzene ([3,5-(t-Bu)$_2$]-DPPBz) (13.4 mg, 0.015 mmol) and a 0.1 M THF solution of iron chloride $FeCl_3$ (0.15 mL, 0.015 mmol) at 0° C., followed by chlorocycloheptane (66.3 mg, 0.5 mmol). The coupling reaction was performed at 80° C. for 24 hours. After cooling to room temperature, a portion of the reaction mixture was taken out, and the yield of the product was measured by gas chromatography (GC), using undecane as an internal standard. The yield was 94%. The results are shown in the Entry 5 column of Table 8.

TABLE 8

Cycloheptyl-Cl + Ph$_3$Al·nMgCl$_2$ (1.2 equiv) → [FeCl$_3$ (3 mol %), Ligand (3 mol %), THF, 80° C., 24 h] → 1 (Ph-cycloheptane) + 2 (cycloheptene) + 3 (cycloheptane)

| Entry | Ligand | GC Yield (%)[a] 1 | 2 | 3 | Collected Starting Materials (%)[a] |
|---|---|---|---|---|---|
| 1 | None | 33 | 6 | 6 | 52 |
| 2 | DPPBz | 58 | 5 | 6 | 30 |
| 3 | [4-MeO]-DPPBz | 83 | 1 | 4 | 7 |
| 4 | [3,5-Me$_2$]-DPPBz | 86 | 1 | 3 | 7 |
| 5 | [3,5-(t-Bu)$_2$]-DPPBz[b] | 95 | 1 | 5 | 0 |
| 6 | [3,5-(TMS)$_2$]-DPPBz | 94 | 1 | 3 | 0 |

[a]The yield was measured by calibrated GC analysis using undecane as an internal standard.
[b]About 2% of Bi(cycloheptane) was produced.

Example 11

Cross-Coupling Reaction (Organoaluminum Reagent)

The following reactions were performed as in Entry 5 of Example 10. The yields of Entries 1 and 2 were measured by $^1$H-NMR using 1,1,2,2-tetrachloroethane as an internal standard. The yield of Entry 3 was measured by $^1$H-NMR using pyrazine as an internal standard.

TABLE 9

Ph$_3$Al·nMgCl$_2$ + Cl-(CH$_2$)$_n$-OH → [FeCl$_3$ (3 mol %), Ligand (3 mol %), THF, 80° C., t h] → Ph-(CH$_2$)$_n$-OH

| Entry | Ligand | t (h) | Yield (%) | Collected Starting Materials (%) |
|---|---|---|---|---|
| 1[a] | DPPBz | 24 | 30 | 55 |
| 2[a] | [3,5-(t-Bu)$_2$]-DPPBz | 12 | 84 | 8 |
| 3[b] | [3,5-(TMS)$_2$]-DPPBz | 12 | 94 | 3 |

[a]The yield was determined by $^1$H NMR using 1,1,2,2-tetrachloroethane as an internal standard.
[b]The yield was determined by $^1$H NMR using pyrazine as an internal standard.

Example 12

Cross-Coupling Reaction (Organoaluminum Reagent)

The following reactions were performed as in Entry 5 of Example 10 The yields of Entries 1 and 2 were measured by $^1$H-NMR using 1,1,2,2-tetrachloroethane as an internal standard. The yield of Entry 3 was obtained by isolating the target compound after column chromatography.

TABLE 10

Ph$_3$Al·nMgCl$_2$ + Br-(CH$_2$)$_5$-C(O)-OEt → [FeCl$_3$ (3 mol %), Ligand (3 mol %), THF, 80° C., 48 h] → Ph-(CH$_2$)$_5$-C(O)-OEt

| entry | Ligand | yield[a] (%) | RSM[a] (%) |
|---|---|---|---|
| 1 | DPPBz | 67 | 12 |
| 2 | [3,5-(t-Bu)$_2$]-DPPBz | 71 | 11 |
| 3 | [3,5-(TMS)$_2$]-DPPBz | 87[b] | trace |

[a]The yield was determined by $^1$H NMR using 1,1,2,2-tetrachloroethane as an internal standard.
[b]Isolated yield.

The invention claimed is:

1. A bisphosphine compound represented by Formula (4b):

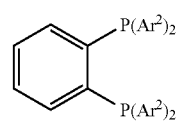

(4b)

wherein each Ar² is independently a group represented by the formula:

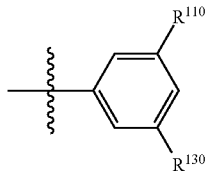

wherein $R^{110}$ and $R^{130}$ are each independently a $C_3$-$C_6$ alkyl, $C_1$-$C_6$ alkoxy, or tri($C_1$-$C_6$)alkylsilyl group.

2. The bisphosphine compound according to claim 1, wherein each Ar² is independently selected from a group consisting of the formula:

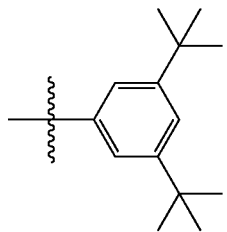 or 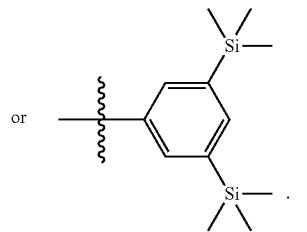

3. A process for producing a bisphosphine compound represented by Formula (4b):

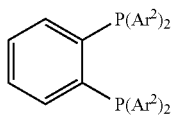

(4b)

wherein each Ar² is independently a group represented by the formula:

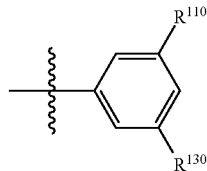

wherein $R^{110}$ and $R^{130}$ are each independently a $C_3$-$C_6$ alkyl, $C_1$-$C_6$ alkoxy, or tri($C_1$-$C_6$)alkylsilyl group;

the process comprising:

reacting a compound represented by Formula (6):

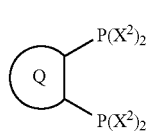

(6)

wherein each X² is a halogen atom, and Q is an unsubstituted 1,2-phenylene, with a metal reagent represented by Formula (7):

Ar²-M (7)

wherein M is Li or a group represented by the formula: MgY¹, with Y¹ being a halogen atom, and Ar² is as defined above.

* * * * *